United States Patent [19]

Blake et al.

[11] Patent Number: 5,439,808
[45] Date of Patent: Aug. 8, 1995

[54] **METHOD FOR THE HIGH LEVEL EXPRESSION, PURIFICATION AND REFOLDING OF THE OUTER MEMBRANE GROUP B PORIN PROTEINS FROM *NEISSERIA MENINGITIDIS***

[75] Inventors: Milan S. Blake, New York, N.Y.;
Joseph Y. Tai, Fort Washington, Pa.;
Huilin L. Qi, New York, N.Y.;
Shu-Mei Liang, Bethesda; Lucjan J. J. Hronowski, Laurel, both of Md.;
Jeffrey K. Pullen, Columbia, Md.

[73] Assignees: North American Vaccine, Inc., Beltsville, Md.; The Rockefeller University, New York, N.Y.

[21] Appl. No.: 96,182

[22] Filed: Jul. 23, 1993

[51] Int. Cl.$^6$ .................. C12N 15/31; C12N 15/62; C12N 15/67; C12N 15/70
[52] U.S. Cl. .................. 435/69.1; 435/69.3; 435/69.7; 435/172.3; 435/252.33; 435/320.1; 435/844; 530/417; 935/10; 935/12; 935/29; 935/73
[58] Field of Search .............. 435/252.3, 252.33, 69.1; 530/350, 403, 417; 424/92, 93 A

[56] References Cited

U.S. PATENT DOCUMENTS

| | | | |
|---|---|---|---|
| 4,134,214 | 1/1979 | Graham et al. | 34/5 |
| 4,271,147 | 6/1981 | Helting et al. | 424/92 |
| 4,356,170 | 10/1982 | Jennings et al. | 424/92 |
| 4,451,446 | 5/1984 | Vandevelde et al. | 424/92 |
| 4,727,136 | 2/1988 | Jennings et al. | 530/395 |

FOREIGN PATENT DOCUMENTS

| | | |
|---|---|---|
| 0338265A2 | 10/1989 | European Pat. Off. |
| 0351604A1 | 1/1990 | European Pat. Off. |
| 0467714A1 | 1/1992 | European Pat. Off. |
| 0468714A2 | 1/1992 | European Pat. Off. |
| 0474313A2 | 3/1992 | European Pat. Off. |
| 0492964 | 7/1992 | European Pat. Off. |
| 0519554A1 | 12/1992 | European Pat. Off. |
| WO90/06696 | 6/1990 | WIPO |
| WO90/11777 | 10/1990 | WIPO |
| WO91/04049 | 4/1991 | WIPO |
| WO92/01001 | 1/1992 | WIPO |
| WO92/01460 | 2/1992 | WIPO |
| WO92/03467 | 3/1992 | WIPO |
| WO92/16230 | 10/1992 | WIPO |

OTHER PUBLICATIONS

Ashton, F. E. et al., Protective efficacy of mouse serum to the N-propionyl derivative of meningococcal group B polysaccharide, *Microbial Pathog.* 6:455-458 (1989).

Barlow, A. K. et al., Molecular Cloning and Expression of *Neisseria meningitidis* Class 1 Outer Membrane Protein in *Escherichia coli* K-12, *Infect. Immun.* 55:2734-2740 (1987).

Bjornson et al., Endotoxin-Associated Protein: a Potent Stimulus for Human Granulocytopoietic Activity Which May Be Accessory Cell Independant, *Infect. Immun.* 56:1602-1607 (1988).

Blake, M. S. et al., Protein III: Structure, Function, and Genetics, *Clin. Microbiol. Rev.* 2(Suppl.):S60-S63 (1989).

Boons, G. J. P. H. et al., Preparation of a Well-Defined Sugar-Peptide Conjugate: A Possible Approach to a Synthetic Vaccine Against *Neisseria meningitidis, Bioorganic & Medicinal Chemistry Letters* 1:303-308 (1991).

(List continued on next page.)

Primary Examiner—Robert A. Wax
Assistant Examiner—William W. Moore
Attorney, Agent, or Firm—Sterne, Kessler, Goldstein & Fox

[57] ABSTRACT

The present invention relates, in general, to a method for the high level expression of the outer membrane protein meningococcal group B porin proteins and fusion proteins thereof. In particular, the present invention relates to a method of expressing the outer membrane protein meningococcal group B porin proteins in *E. coli* wherein the meningococcal group B porin proteins yard fusion proteins thereof comprise more than 2% of the total protein expressed in *E. coli*. The invention also relates to a method of purification and refolding of the meningococcal group B porin proteins and fusion proteins thereof and to their use in vaccines.

19 Claims, 17 Drawing Sheets

OTHER PUBLICATIONS

Bremer, E. et al., Isolation and characterization of mutants deleted for the *sulA-ompA* region of the *Escherichia coli* K-12 chromosome, *FEMS Microbiol. Lett.* 33:173–178 (1986).

Cowan, S. W. et al., Crystal structures explain functional properties of two *E. coli* porins, *Nature* 358:727–733 (1992).

Feavers, I. M. et al., Molecular Analysis of the Serotyping Antigens of *Neisseria meningitidis*, *Infect. Immun.* 60:3620–3629 (1992).

Frasch, C. E. et al., Serotype Antigens of *Neisseria meningitidis* and a Proposed Scheme for Designation of Serotypes, *Rev. Infect. Dis.* 7:504–510 (1985).

Frasch, C. E., Production and Control of *Neisseria meningitidis* Vaccines, in *Bacterial Vaccines*, Alan R. Liss, Inc., pp. 123–145 (1990).

Freudl, R. et al., A Lower Size Limit Exists for Export of Fragments of an Outer Membrane Protein (OmpA) of *Escherichia coli* K-12, *J. Mol. Biol.* 205:771–775 (1989).

Gotschlich, E. C. et al., Gonococcal protein III. Purification and chemical characterization of the protein, and the DNA sequence of the structural gene, *Antonie van Leeuwenhoek* 53:455–459 (1987).

Holzenburg, A. et al., Rapid Isolation of OmpF Porin-LPS Complexes Suitable for Structure-Function Studies, *Biochemistry* 28:4187–4193 (1989).

James, L. T. et al., An Improved Method for the Isolation of the Major Protein of the Gonococcal Outer Membrane in an Antigenically Reactive Form, *J. Immunol. Meth.* 42:223–228 (1981).

Jennings, H. J., Capsular Polysaccharides as Vaccine Candidates, *Current Topics in Microbiology and Immunology* 150:105–107 (1990).

Jennings, H. J. et al., Determinant Specificities of the Groups B and C Polysaccharides of *Neisseria meningitidis*, *J. Immunol.* 134:2651–2657 (1985).

Jennings, H. J. et al., Induction of Meningococcal Group B Polysaccharide-Specific IgG Antibodies in Mice by Using an N-Propionylated B Polysaccharide-Tetanus Toxoid Conjugate Vaccine, *J. Immunol.* 137:1708–1713 (1986).

Jennings, H. J. et al., Unique Intermolecular Bacterial Epitope Involving the Homosialopolysaccharide Capsule on the Cell Surface of Group B *Neisseria meningitidis* and *Escherichia coli* K1, *J. Immunol.* 142:3585–3591 (1989).

Jones, R. B. et al., Resolution of Basic Gonococcal Outer Membrane Proteins by Nonequilibrium pH Gradient Electrophoresis, *Infect. Immun.* 30:773–780 (1980).

Klose, M. et al., Internal Deletions in the Gene for an *Escherichia coli* Outer Membrane Protein Define an Area Possibly Important for Recognition of the Outer membrane by This Polypeptide, *J. Biol. Chem.* 263:13291–13296 (1988).

Klose, M. et al., The Influence of Amino Substitutions within the Mature Part of an *Escherichia coli* Outer Membrane Protein (OmpA) on Assembly of the Polypeptide into Its Membrane, *J. Biol. Chem.* 263:13297–13302 (1988).

McGuinness, B. et al., Deduced Amino Acid Sequences of Class 1 Protein (PorA) From Three Strains of *Neisseria meningitidis*, *J. Exp. Med.* 171:1871–1882 (1990).

Murakami, K. et al., Cloning and Characterization of the Structural Gene for the Class 2 Protein of *Neisseria meningitidis*, *Infect. Immun.* 57:2318–2323 (1989).

Novagen Technical Bulletin: Plasmid map of pET-1-1a(1990).

Poolman, J. T. et al., Class 1/3 Outer Membrane Protein Vaccine Against Group B, Type 15, Subtype 16 Meningococci, *Develop. Biol. Standard.* 63:147–152 (1986).

Poolman, J. T. et al., Purification, Cyanogen Bromide Cleavage, and Amino Terminus Sequencing of Class 1 and Class 3 Outer Membrane Proteins of Meningococci, *Infect. Immun.* 57:1005–1007 (1989).

Poolman, J. T. Polysaccharides and Membrane Vaccines, in *Bacterial Vaccines*, Alan R. Liss, Inc., pp. 57–86 (1990).

Saukkonen, K. et al., Comparative evaluation of potential components for group B meningococcal vaccine by passive protection in the infant rat and in vitro bactericidal assay, *Vaccine* 7:325–328 (1989).

(List continued on next page.)

OTHER PUBLICATIONS

Sen, K. et al., Trimerization of an in Vitro Synthesized OmpF Porin of *Escherichia coli* Outer Membrane, *J. Biol. Chem.* 266:11295–11300 (1991).

Studier et al., Use of Bacteriophage T7 RNA Polymerase to Direct Selective High-level Expression of Cloned Genes, *J. Mol. Biol.* 189:113–130 (1986).

van der Ley, P. et al., Topology of Outer Membrane Porins in Pathogenic Neissria spp., *Infect. Immun.* 59:2963–2971 (1991).

Verheul, A. F. M. et al., Preparation, Characterization, and Immunogenicity of Meningococcal Immunotype L2 and L3, 7, 9 Phosphoethanolamine Group–Containing Oligosaccharide–Protein Conjugates, *Infect. Immun.* 59:843–851 (1991).

Ward, M. J. et al., Sequence analysis and relationships between meningococcal class 3 serotype proteins and other porins from pathogenic and non–pathogenic Neisseria Species, *FEMS Microbiol. Lett.* 94:283–289 (1992).

Wolff, K. et al., The class 3 outer membrane protein (PorB) of *Neisseria meningitidis*: gene sequence and homology to the gonococcal porin PIA, *FEMS Microbiol. Lett.* 83:179–185 (1991).

Young, J. D. E. et al., Functional channel formation associated with cytotoxic T–cell granules, *Proc. Natl. Acad. Sci. USA* 83:150–154 (1986).

Carbonetti, N. H., et al., 1987, Proceedings of the National Academy of Sciences, U.S.A., 84: 9084–9088.

Zapata, G. A., et al., 1992, Molecular Microbiology, 6(23): 3493–3499.

Müller, N., et al., 1989, Molecular and Biochemical Parasitology, 36:151–160.

Blake, M. S., et al., 1984, Journal of Experimental Medecine, 159: 452–462.

Gotschlich, E. C., et al., 1987, Journal of Experimental Medecine, 165: 471–482.

Lin, S.-W., et al., 1987, Biochemistry, 26: 5267–5274.

Marston, F., 1986, Biochemical Journal 240(1): 1–12.

Lehnhardt, S., et al., 1987, The Journal of Biological Chemistry, 262(4): 1716–1719.

Novagen, Inc., Products Catalogue, 1993, pp. 1 and 36–47, (Novagen, Inc., 597 Science Drive, Madison, Wis. 53711).

Kroll, D. J., et al., 1993, DNA and Cell Biology, 12(5): 441–453.

Morona, R., et al., 1985, Molecular and General Genetics, 201: 357–359.

Dalbey, R. E., et al., 1985, The Journal of Biological Chemistry, 260(29): 15925–15931.

de Cock, H., et al., 1990, The Journal of Biological Chemistry, 265(8): 4646–4651.

Freudl, R., et al., 1987, Journal of Bacteriology, 169(1): 66–71.

Barik, S., et al., 1991, Journal of Virology, 65(4): 1719–1726.

Bremer, E., et al., 1982, European Journal of Biochemistry, 122: 231.

Freudl, R., et al., 1986, Journal of Molecular Biology, 188(3): 491–494.

Furlong, J., et al., 1991, Virology, 182(2): 846–851.

He, X.-S., et al., 1991, Biochemical and Biophysical Research Communications, 180(2): 994–1001.

Reid, J., et al., 1988 The Journal of Biological Chemistry, 263(16): 994–1001.

```
                C   C
                _   _
TTG TAC GGT ACA ATT AAA GCA GGC GTA GAA ACT TCC CGC TCT GTA TTT        48
Leu Tyr Gly Thr Ile Lys Ala Gly Val Glu Thr Ser Arg Ser Val Phe
 1           5            10               15
CAC CAG AAC GGC CAA GTT ACT GAA GTT ACA ACC GCT ACC GGC ATC GTT        96

His Gln Asn Gly Gln Val Thr Glu Val Thr Thr Ala Thr Gly Ile Val
             20               25              30

GAT TTG GGT TCG AAA ATC GGC TTC AAA GGC CAA GAA GAC CTC GGT AAC       144

Asp Leu Gly Ser Lys Ile Gly Phe Lys Gly Gln Glu Asp Leu Gly Asn
             35              40              45

GGC CTG AAA GCC ATT TGG CAG GTT GAG CAA AAA GCA TCT ATC GCC GGT       192
Gly Leu Lys Ala Ile Trp Gln Val Glu Gln Lys Ala Ser Ile Ala Gly
     50              55              60

ACT GAC TCC GGT TGG GGC AAC CGC CAA TCC TTC ATC GGC TTG AAA GGC       240
Thr Asp Ser Gly Trp Gly Asn Arg Gln Ser Phe Ile Gly Leu Lys Gly
 65              70              75              80

GGC TTC GGT AAA TTG CGC GTC GGT CGT TTG AAC AGC GTC CTG AAA GAC       288
Gly Phe Gly Lys Leu Arg Val Gly Arg Leu Asn Ser Val Leu Lys Asp
                 85              90              95

ACC GGC GAC ATC AAT CCT TGG GAT AGC AAA AGC GAC TAT TTG GGT GTA       336
Thr Gly Asp Ile Asn Pro Trp Asp Ser Lys Ser Asp Tyr Leu Gly Val
             100             105             110

AAC AAA ATT GCC GAA CCC GAG GCA CGC CTC ATT TCC GTA CGC TAC GAT       384
Asn Lys Ile Ala Glu Pro Glu Ala Arg Leu Ile Ser Val Arg Tyr Asp
         115             120             125

TCT CCC GAA TTT GCC GGC CTC AGC GGC AGC GTA CAA TAC GCC CTT AAC       432
Ser Pro Glu Phe Ala Gly Leu Ser Gly Ser Val Gln Tyr Ala Leu Asn
 130             135             140

GAC AAT GCA GGC AGA CAT AAC AGC GAA TCT TAC CAC GCC GGC TTC AAC       480
Asp Asn Ala Gly Arg His Asn Ser Glu Ser Tyr His Ala Gly Phe Asn
145             150             155             160
```

FIG.4A

```
TAC AAA AAC GGT GGC TTC TTC GTG CAA TAT GGC GGT GCC TAT AAA AGA         528
Tyr Lys Asn Gly Gly Phe Phe Val Gln Tyr Gly Gly Ala Tyr Lys Arg
            165                 170                 175

CAT CAT CAA GTG CAA GAG GGC TTG AAT ATT GAG AAA TAC CAG ATT CAC         576
His His Gln Val Gln Glu Gly Leu Asn Ile Glu Lys Tyr Gln Ile His
            180                 185                 190

CGT TTG GTC AGC GGT TAC GAC AAT GAT GCC CTG TAC GCT TCC GTA GCC         624
Arg Leu Val Ser Gly Tyr Asp Asn Asp Ala Leu Tyr Ala Ser Val Ala
            195                 200                 205

GTA CAG CAA CAA GAC GCG AAA CTG ACT GAT GCT TCC AAT TCG CAC AAC         672
Val Gln Gln Gln Asp Ala Lys Leu Thr Asp Ala Ser Asn Ser His Asn
            210                 215                 220

TCT CAA ACC GAA GTT GCC GCT ACC TTG GCA TAC CGC TTC GGC AAC GTA         720
Ser Gln Thr Glu Val Ala Ala Thr Leu Ala Tyr Arg Phe Gly Asn Val
225                 230                 235                 240

ACG CCC CGA GTT TCT TAC GCC CAC GGC TTC AAA GGT TTG GTT GAT GAT         768
Thr Pro Arg Val Ser Tyr Ala His Gly Phe Lys Gly Leu Val Asp Asp
            245                 250                 255

GCA GAC ATA GGC AAC GAA TAC GAC CAA GTG GTT GTC GGT GCG GAA TAC         816
Ala Asp Ile Gly Asn Glu Tyr Asp Gln Val Val Val Gly Ala Glu Tyr
            260                 265                 270

GAC TTC TCC AAA CGC ACT TCT GCC TTG GTT TCT GCC GGT TGG TTG CAA         864
Asp Phe Ser Lys Arg Thr Ser Ala Leu Val Ser Ala Gly Trp Leu Gln
            275                 280                 285

GAA GGC AAA GGC GAA AAC AAA TTC GTA GCG ACT GCC GGC GGT GTT GGT         912
Glu Gly Lys Gly Glu Asn Lys Phe Val Ala Thr Ala Gly Gly Val Gly
            290                 295                 300

CTG CGT CAC AAA TTC TAA                                                 930
Leu Arg His Lys Phe
305                 310
                            FIG.4B
```

```
ATG GAC GTT ACC TTG TAC GGT ACA ATT AAA GCA GGC GTA GAA GTT TCT        48
Met Asp Val Thr Leu Tyr Gly Thr Ile Lys Ala Gly Val Glu Val Ser
 1               5                  10                 15

CGC GTA AAA GAT GCT GGT ACA TAT AAA GCT CAA GGC GGA AAA TCT AAA        96
Arg Val Lys Asp Ala Gly Thr Tyr Lys Ala Gln Gly Gly Lys Ser Lys
             20                  25                 30

ACT GCA ACC CAA ATT GCC GAC TTC GGT TCT AAA ATC GGT TTC AAA GGT       144
Thr Ala Thr Gln Ile Ala Asp Phe Gly Ser Lys Ile Gly Phe Lys Gly
             35                  40                 45

CAA GAA GAC CTC GGC AAC GGC ATG AAA GCC ATT TGG CAG TTG GAA CAA       192
Gln Glu Asp Leu Gly Asn Gly Met Lys Ala Ile Trp Gln Leu Glu Gln
         50                  55                     60

AAA GCC TCC ATC GCC GGC ACT AAC AGC GGC TGG GGT AAC CGC CAG TCC       240
Lys Ala Ser Ile Ala Gly Thr Asn Ser Gly Trp Gly Asn Arg Gln Ser
 65                  70                  75                 80

TTC ATC GGC TTG AAA GGC GGC TTC GGT ACC GTC CGC GCC GGT AAT CTG       288
Phe Ile Gly Leu Lys Gly Gly Phe Gly Thr Val Arg Ala Gly Asn Leu
                 85                  90                 95

AAC ACC GTA TTG AAA GAC AGC GGC GAC AAC GTC AAT GCA TGG GAA TCT       336
Asn Thr Val Leu Lys Asp Ser Gly Asp Asn Val Asn Ala Trp Glu Ser
                100                 105                110

GGT TCT AAC ACC GAA GAT GTA CTG GGA CTG GGT ACT ATC GGT CGT GTA       384
Gly Ser Asn Thr Glu Asp Val Leu Gly Leu Gly Thr Ile Gly Arg Val
            115                 120                 125

GAA AGC CGT GAA ATC TCC GTA CGC TAC GAC TCT CCC GTA TTT GCA GGC       432
Glu Ser Arg Glu Ile Ser Val Arg Tyr Asp Ser Pro Val Phe Ala Gly
            130                 135                 140

TTC AGC GGC AGC GTA CAA TAC GTT CCG CGC GAT AAT GCG AAT GAT GTG       480
Phe Ser Gly Ser Val Gln Tyr Val Pro Arg Asp Asn Ala Asn Asp Val
145                 150                 155                160
```

FIG.9A

```
GAT AAA TAC AAA CAT ACG AAG TCC AGC CGT GAG TCT TAC CAC GCC GGT       528
Asp Lys Tyr Lys His Thr Lys Ser Ser Arg Glu Ser Tyr His Ala Gly
            165             170             175

CTG AAA TAC GAA AAT GCC GGT TTC TTC GGT CAA TAC GCA GGT TCT TTT       576
Leu Lys Tyr Glu Asn Ala Gly Phe Phe Gly Gln Tyr Ala Gly Ser Phe
            180             185             190

GCC AAA TAT GCT GAT TTG AAC ACT GAT GCA GAA CGT GTT GCA GTA AAT       624
Ala Lys Tyr Ala Asp Leu Asn Thr Asp Ala Glu Arg Val Ala Val Asn
            195             200             205

ACT GCA AAT GCC CAT CCT GTT AAG GAT TAC CAA GTA CAC CGC GTA GTT       672
Thr Ala Asn Ala His Pro Val Lys Asp Tyr Gln Val His Arg Val Val
            210             215             220

GCC GGT TAC GAT GCC AAT GAC CTG TAC GTT TCT GTT GCC GGT CAG TAT       720
Ala Gly Tyr Asp Ala Asn Asp Leu Tyr Val Ser Val Ala Gly Gln Tyr
225             230             235             240

GAA GCT GCT AAA AAC AAC GAG GTT GGT TCT ACC AAG GGT AAA AAA CAC       768
Glu Ala Ala Lys Asn Asn Glu Val Gly Ser Thr Lys Gly Lys Lys His
            245             250             255

GAG CAA ACT CAA GTT GCC GCT ACT GCC GCT TAC CGT TTT GGC AAC GTA       816
Glu Gln Thr Gln Val Ala Ala Thr Ala Ala Tyr Arg Phe Gly Asn Val
            260             265             270

ACG CCT CGC GTT TCT TAC GCC CAC GGC TTC AAA GCT AAA GTG AAT GGC       864
Thr Pro Arg Val Ser Tyr Ala His Gly Phe Lys Ala Lys Val Asn Gly
            275             280             285

GTG AAA GAC GCA AAT TAC CAA TAC GAC CAA GTT ATC GTT GGT GCC GAC       912
Val Lys Asp Ala Asn Tyr Gln Tyr Asp Gln Val Ile Val Gly Ala Asp
            290             295             300

TAC GAC TTC TCC AAA CGC ACT TCC GCT CTG GTT TCT GCC GGT TGG TTG       960
Tyr Asp Phe Ser Lys Arg Thr Ser Ala Leu Val Ser Ala Gly Trp Leu
305             310             315             320
```

FIG.9B

```
AAA CAA GGT AAA GGC GCG GGA AAA GTC GAA CAA ACT GCC AGC ATG GTT        1008
Lys Gln Gly Lys Gly Ala Gly Lys Val Glu Gln Thr Ala Ser Met Val
            325                 330                 335

GGT CTG CGT CAC AAA TTC TAA                                           1029
Gly Leu Arg His Lys Phe
        340
```

FIG.9C

```
ATG GCT AGC ATG ACT GGT GGA CAG CAA ATG GGT CGG GAT TCA AGC TTG      48
Met Ala Ser Met Thr Gly Gly Gln Gln Met Gly Arg Asp Ser Ser Leu
 1           5                  10                 15

GTA CCG AGC TCG GAT CCA GAC GTT ACC TTG TAC GGT ACA ATT AAA GCA      96
Val Pro Ser Ser Asp Pro Asp Val Thr Leu Tyr Gly Thr Ile Lys Ala
                 20                 25                 30

GGC GTA GAA GTT TCT CGC GTA AAA GAT GCT GGT ACA TAT AAA GCT CAA     144
Gly Val Glu Val Ser Arg Val Lys Asp Ala Gly Thr Tyr Lys Ala Gln
             35                 40                 45

GGC GGA AAA TCT AAA ACT GCA ACC CAA ATT GCC GAC TTC GGT TCT AAA     192
Gly Gly Lys Ser Lys Thr Ala Thr Gln Ile Ala Asp Phe Gly Ser Lys
         50                 55                 60

ATC GGT TTC AAA GGT CAA GAA GAC CTC GGC AAC GGC ATG AAA GCC ATT     240
Ile Gly Phe Lys Gly Gln Glu Asp Leu Gly Asn Gly Met Lys Ala Ile
65          70                 75                 80

TGG CAG TTG GAA CAA AAA GCC TCC ATC GCC GGC ACT AAC AGC GGC TGG     288
Trp Gln Leu Glu Gln Lys Ala Ser Ile Ala Gly Thr Asn Ser Gly Trp
                 85                 90                 95

GGT AAC CGC CAG TCC TTC ATC GGC TTG AAA GGC GGC TTC GGT ACC GTC     336
Gly Asn Arg Gln Ser Phe Ile Gly Leu Lys Gly Gly Phe Gly Thr Val
             100                105                110

CGC GCC GGT AAT CTG AAC ACC GTA TTG AAA GAC AGC GGC GAC AAC GTC     384
Arg Ala Gly Asn Leu Asn Thr Val Leu Lys Asp Ser Gly Asp Asn Val
         115                120                125

AAT GCA TGG GAA TCT GGT TCT AAC ACC GAA GAT GTA CTG GGA CTG GGT     432
Asn Ala Trp Glu Ser Gly Ser Asn Thr Glu Asp Val Leu Gly Leu Gly
     130                135                140

ACT ATC GGT CGT GTA GAA AGC CGT GAA ATC TCC GTA CGC TAC GAC TCT     480
Thr Ile Gly Arg Val Glu Ser Arg Glu Ile Ser Val Arg Tyr Asp Ser
145             150                155                160
```

FIG.10A

```
CCC GTA TTT GCA GGC TTC AGC GGC AGC GTA CAA TAC GTT CCG CGC GAT      528
Pro Val Phe Ala Gly Phe Ser Gly Ser Val Gln Tyr Val Pro Arg Asp
            165                 170                 175

AAT GCG AAT GAT GTG GAT AAA TAC AAA CAT ACG AAG TCC AGC CGT GAG      576
Asn Ala Asn Asp Val Asp Lys Tyr Lys His Thr Lys Ser Ser Arg Glu
            180                 185                 190

TCT TAC CAC GCC GGT CTG AAA TAC GAA AAT GCC GGT TTC TTC GGT CAA      624
Ser Tyr His Ala Gly Leu Lys Tyr Glu Asn Ala Gly Phe Phe Gly Gln
            195                 200                 205

TAC GCA GGT TCT TTT GCC AAA TAT GCT GAT TTG AAC ACT GAT GCA GAA      672
Tyr Ala Gly Ser Phe Ala Lys Tyr Ala Asp Leu Asn Thr Asp Ala Glu
            210                 215                 220

CGT GTT GCA GTA AAT ACT GCA AAT GCC CAT CCT GTT AAG GAT TAC CAA      720
Arg Val Ala Val Asn Thr Ala Asn Ala His Pro Val Lys Asp Tyr Gln
225             230                 235                 240

GTA CAC CGC GTA GTT GCC GGT TAC GAT GCC AAT GAC CTG TAC GTT TCT      768
Val His Arg Val Val Ala Gly Tyr Asp Ala Asn Asp Leu Tyr Val Ser
                245                 250                 255

GTT GCC GGT CAG TAT GAA GCT GCT AAA AAC AAC GAG GTT GGT TCT ACC      816
Val Ala Gly Gln Tyr Glu Ala Ala Lys Asn Asn Glu Val Gly Ser Thr
            260                 265                 270

AAG GGT AAA AAA CAC GAG CAA ACT CAA GTT GCC GCT ACT GCC GCT TAC      864
Lys Gly Lys Lys His Glu Gln Thr Gln Val Ala Ala Thr Ala Ala Tyr
            275                 280                 285

CGT TTT GGC AAC GTA ACG CCT CGC GTT TCT TAC GCC CAC GGC TTC AAA      912
Arg Phe Gly Asn Val Thr Pro Arg Val Ser Tyr Ala His Gly Phe Lys
            290                 295                 300

GCT AAA GTG AAT GGC GTG AAA GAC GCA AAT TAC CAA TAC GAC CAA GTT      960
Ala Lys Val Asn Gly Val Lys Asp Ala Asn Tyr Gln Tyr Asp Gln Val
305             310                 315                 320
```

FIG.10B

```
ATC GTT GGT GCC GAC TAC GAC TTC TCC AAA CGC ACT TCC GCT CTG GTT        1008
Ile Val Gly Ala Asp Tyr Asp Phe Ser Lys Arg Thr Ser Ala Leu Val
            325                 330                 335

TCT GCC GGT TGG TTG AAA CAA GGT AAA GGC GCG GGA AAA GTC GAA CAA        1056
Ser Ala Gly Trp Leu Lys Gln Gly Lys Gly Ala Gly Lys Val Glu Gln
            340                 345                 350

ACT GCC AGC ATG GTT GGT CTG CGT CAC AAA TTC TAA                        1092
Thr Ala Ser Met Val Gly Leu Arg His Lys Phe
            355             360
```

FIG.10C

```
         BglII                                         XbaI
         ────                                          ───
         AGATCTCGAT CCCGCGAAAT TAATACGACT CACTATAGGG AGACCACAAC GGTTTCCCTC    60

NboI    NbeI
                                           ────    ────
         TAGAAATAAT TTTGTTTAAC TTAAAGAAGG AGATATACAT ATG GCT AGC ATG ACT      115
                                                    Met Ala Ser Met Thr
                                                     1               5

HindIII KpnI   SacI  (BamHI)
                                       ─────── ────   ────  ──────
         GGT GGA CAG CAA ATG GGT CGG GAT TCA AGC TTG GTA CCG AGC TCG GAT      163
         Gly Gly Gln Gln Met Gly Arg Asp Ser Ser Leu Val Pro Ser Ser Asp
                          10              15                  20

CTG CAG GTT ACC TTG TAC GGT ACA                                      187
         Leu Gln Val Thr Leu Tyr Gly Thr
                          25
                        ──────────────►

─────────────── XbaI
                         ◄───────────────────
         GTT GGT CTG CGT CAC AAA TTC TAACTCGAGC AGATCCGGCT GCTAACAAAG          51
         Val Gly Leu Arg His Lys Phe
          1           5

CCC                                                                   54
```

FIG.11B

METHOD FOR THE HIGH LEVEL EXPRESSION, PURIFICATION AND REFOLDING OF THE OUTER MEMBRANE GROUP B PORIN PROTEINS FROM *NEISSERIA MENINGITIDIS*

BACKGROUND OF THE INVENTION

1. Field of the Invention

The present invention is in the field of recombinant genetics, protein expression, and vaccines. The present invention relates, in particular, to a method of expressing in a recombinant host an outer membrane group B porin protein from *Neisseria meningitidis*. The invention also relates to a method of purification and refolding of the recombinant protein.

2. Background Information

The outer membranes of Neisseria species much like other Gram negative bacteria are semi-permeable membranes which allow free flow access annd escape of small molecular weight substances to and from the periplasmic space of these bacteria but retard molecules of larger size (Heasley, F. A., et al., "Reconstitution and characterization of the *N. gonorrhoeae* outer membrane permeability barrier," in *Genetics and Immunobiology of Neisseria gonorrhoeae*, Danielsson and Nomark, eds., University of Umea, Umea, pp. 12–15 (1980); Douglas, J. T., et at., *FEMS Microbiol. Lett.* 12:305–309 (1981)). One of the mechanisms whereby this is accomplished is the inclusion within these membranes of proteins which have been collectively named porins. These proteins are made up of three identical polypeptide chains (Jones, R. B., et at., *Infect. Immun.* 30:773–780 (1980); McDade, Jr. and Johnston, *J. Bacteriol.* 141:1183–1191 (1980)) and in their native trimer conformation, form water filled, voltage-dependent channels within the outer membrane of the bacteria or other membranes to which they have been introduced (Lynch, E. C., et al., *Biophys. J.* 41:62 (1983); Lynch, E. C., et al., *Biophys. J.* 45:104–107 (1984); Young, J. D. E., et at., *Proc. Natl. Acad. Sci.* USA 80:3831–3835 (1983); Mauro, A., et al., *Proc. Natl. Acad. Sci.* USA 85:1071–1075 (1988); Young, J. D., et al., *Proc. Natl. Acad. Sci.* USA 83:150–154 (1986)). Because of the relative abundance of these proteins within the outer membrane, these protein antigens have also been used to subgroup both *Neisseria gonorrhoeae* and *Neisseria meningitidis* into several serotypes for epidemiological purposes (Frasch, C. E., et al., *Rev. Infect. Dis.* 7:504–510 (1985); Knapp, J. S., et al., "Overview of epidemiological and clinical applications of auxotype/-serovar classification of *Neisseria gonorrhoeae*," *The Pathogenic Neisseriae*, Schoolnik, G. K., ed., American Society for Microbiology, Washington, pp. 6–12 (1985)). To date, many of these proteins from both gonococci and meningococci have been purified (Heckels, J. E., *J. Gen. Microbiol.* 99:333–341 (1977); James and Heckels, *J. Immunol. Meth.* 42:223–228 (1981); Judd, R. C., *Anal. Biochem.* 173:307–316 (1988); Blake and Gotschlich, *Infect. Immun.* 36:277–283 (1982); Wetzler, L. M., et al., *J. Exp. Med.* 168:1883–1897 (1988)), and cloned and sequenced (Gotschlich, E. C., et al., *Proc. Natl. Acad. Sci.* USA 84:8135–8139 (1987); McGuinness, B., et al., *J. Exp. Med.* 171:1871–1882 (1990); Carbonetti and Sparling, *Proc. Natl. Acad. Sci.* USA 84:9084–9088 (1987); Feavers, I. M., el at., *Infect. Immun.* 60:3620–3629 (1992); Murakami, K., et al., *Infect. Immun.* 57:2318–2323 (1989); Wolff and Stem, *FEMS Microbiol. Lett.* 83:179–186 (1991); Ward, M. J., et al., *FEMS Microbiol. Lett.* 73:283–289 (1992)).

The porin proteins were initially co-isolated with lipopolysaccharides. Consequently, the porin proteins have been termed "endotoxin-associated proteins" (Bjornson et al., *Infect. Immun.* 56:1602–1607 (1988)). Studies on the wild type porins have reported that full assembly and oligomerization are not achieved unless LPS from the corresponding bacterial strain is present in the protein environment (Holzenburg et al., *Biochemistry* 28:4187–4193 (1989); Sen and Nikaido, *J. Biol. Chem.* 266:11295–11300 (1991)).

The meningococcal porins have been subdivided into three major classifications which in antedated nomenclature were known as Class 1, 2, and 3 (Frasch, C. E., et al., *Rev. Infect. Dis.* 7:504–510 (1985)). Each meningococcus examined has contained one of the alleles for either a Class 2 porin gene or a Class 3 porin gene but not both (Feavers, I. M., et al., *Infect. Immun.* 60:3620–3629 (1992)); Murakami, K., et al., *Infect. Immun.* 57:2318–2323 (1989)). The presence or absence of the Class 1 gene appears to be optional. Likewise, all probed gonococci contain only one porin gene with similarities to either the Class 2 or Class 3 allele (Gotschlich, E. C., et al., *Proc. Natl. Acad. Sci.* USA 84:8135–8139 (1987); Carbonetti and Sparling, *Proc. Natl. Acad. Sci.* USA 84:9084–9088 (1987)). *N. gonorrhoeae* appear to completely lack the Class 1 allele. The data from the genes that have been thus far sequenced would suggest that all neisserial porin proteins have at least 70% homology with each other with some variations on a basic theme (Feavers, I. M., et al., *Infect. Immun.* 60:3620–3629 (1992)). It has been suggested that much of the variation seen between these neisserial porin proteins is due to the immunological pressures brought about by the invasion of these pathogenic organisms into their natural host, man. However, very little is known about how the changes in the porin protein sequence effect the functional activity of these proteins.

It has been previously reported that isolated gonococcal porins of the Class 2 allelic type behave electrophysically somewhat differently than isolated gonococcal porins of the Class 3 type in lipid bilayer studies both in regards to their ion selectivity and voltage-dependence (Lynch, E. C., et al., *Biophys.* J. 41:62 (1983); Lynch, E. C., et al., *Biophys.* J. 45:104–107 (1984)). Furthermore, the ability of the different porins to enter these lipid bilayers from intact living bacteria seems to correlate not only with the porin type but also with the neisserial species from which they were donated (Lynch, E. C., et al., *Biophys.* J. 45:104–107 (1984)). It would seem that at least some of these functional attributes could be related to different areas within the protein sequence of the porin. One such functional area, previously identified within all gonococcal Class 2-like proteins, is the site of chymotrypsin cleavage. Upon chymotrypsin digestion, this class of porins lack the ability to respond to a voltage potential and close. Gonococcal Class 3-like porins as well as meningococcal porins lack this sequence and are thus not subject to chymotrypsin cleavage but nonetheless respond by closing to an applied voltage potential (Greco, F., "The formation of channels in lipid bilayers by gonococcal major outer membrane protein," thesis, The Rockefeller University, New York (1981); Greco, F., et al., *Fed. Proc.* 39:1813 (1980)).

The major impediment for such studies has been the ability to easily manipulate the porin genes by modem molecular techniques and obtain sufficient purified protein to carry out the biophysical characterizations of these altered porin proteins. It was early recognized that cloned neisserial porin genes, when expressed in *Escherichia coli*, were lethal to the host *E. coli* (Carbonetti and Sparling, *Proc. Natl. Acad. Sci.* USA 84:9084-9088 (1987); Carbonetti, N. H., et al., *Proc. Natl. Acad. Sci.* USA 85:6841-6845 (1988); Barlow, A. K., et al., *Infect. Immun.* 55:2734-2740 (1987)). Thus, many of these genes were cloned and sequenced as pieces of the whole gene or placed into low copy number plasmids under tight expression control (Carbonetti, N. H., et al., *Proc. Natl. Acad. Sci.* USA 85:6841-6845 (1988)). Under these conditions, even when the entire porin gene was expressed, very little protein accumulated that could be further purified and processed for characterization.

Another tack to this problem which has met with a modicum of success has been to clone the porin genes into a low copy, tightly controlled expression plasmid, introduce modifications to the porin gene, and then reintroduce the modified sequence back into Neisseria (Carbonetti, N. H., et al., *Proc. Natl. Acad. Sci.* USA 85:6841-6845 (1988)). However, this has also been fraught with problems due to the elaborate restriction endonuclease system present in Neisseria, especially gonococci (Davies, J. K., *Clin. Microbiol. Rev.* 2:S78-S82 (1989)).

The present invention is directed to an approach to overcome these difficulties. The DNA sequence of the mature porin proteins, e.g. class 2 and class 3 as well as fusions thereof, my be amplified using the chromosome of the meningococcal bacteria as a template for the PCR reaction. The amplified porin sequences were ligated and cloned into an expression vector containing the T7 promoter. *E. coli* strain BL21 lysogenic for the DE3 lambda phage (Studier and Moffatt, *J. Mol. Biol.* 189:113-130 (1986)), modified to eliminate the ompA gene, was selected as one expression host for the pET-17b plasmid containing the porin gene. Upon induction, large amounts of the meningococcal porin proteins accumulated within the *E. coli* without any obvious lethal effects to the host bacterium. The expressed meningococcal porin proteins were extracted and processed through standard procedures and finally purified by molecular sieve chromatography and ion exchange chromatography. As judged by the protein profile from the molecular sieve chromatography, the recombinant meningococcal porins eluted from the column as trimers. To be certain that no PCR artifacts had been introduced into the meningococcal porin genes to allow for such high expression, the inserted PorB gene sequence was determined. Inhibition ELISA assays were used to give further evidence that the expressed recombinant porin proteins had renatured into their natural antigenic and trimer conformation.

SUMMARY OF THE INVENTION

Porins from different neisserial strains and species have been shown to have differences in both primary amino acid sequence and biophysical characteristics as observed by functional assays. A closer examination of how the changes in the primary amino acid sequence of *Neisseria porin* molecules correlate with these observed biophysical changes has been impeded by the ability to easily manipulate the cloned porin genes by modern molecular techniques and then subsequently obtain enough of the expressed modified porin protein to purify and apply to these biophysical functional assays. In this invention, the gene coding for a mature PorB protein, lacking the neisserial promoter and signal sequence, was cloned into the expression plasmid pET-17b and transformed into *E. coli*. Upon induction, large amounts of the PorB protein was produced.

The expressed porin protein was then manipulated to regenerate its native trimer structure and was then purified. Sufficient purified recombinant porin protein was obtained for further antigenic as well as biophysical characterization. Thus, this sets the stage whereby the biophysical characterization of these neisserial porin proteins can be examined in more detail.

It is a general object of the invention to provide a method of expressing the meningococcal group B porin protein, in particular, the class 2 and class 3 porin proteins.

It is a specific object of the invention to provide a method of expressing the meningococcal group B class 2 or 3 porin protein in *E. coli* comprising:

(a) transforming *E. coli* by a vector comprising a selectable marker and a gene coding for a protein selected from the group consisting of
  (i) a mature porin protein, and
  (ii) a fusion protein comprising a mature porin protein fused to amino acids 1 to 20 of the T7 gene $\phi 10$ capsid protein;

wherein said gene is operably linked to the T7 promoter;

(b) growing the transformed *E. coli* in a culture media containing a selection agent, and (c) inducing expression of said protein;

wherein the protein comprises more than 2% of the total protein expressed in the *E. coli*.

It is another specific object of the invention to provide a method of purifying and refolding a meningococcal group B porin protein and fusion protein produced according to the above-described methods.

It is a further specific object of the invention to provide a vaccine comprising the meningococcal group B porin protein and fusion protein, produced according to the above methods, in an mount effective to elicit protective antibodies in an animal to *Neisseria meningitidis*; and a pharmaceutically acceptable diluent, carrier, or excipient.

It is another specific object of the invention to provide the above-described vaccine, wherein said meningococcal group B porin protein or fusion protein is conjugated to a *Neisseria meningitidis* capsular polysaccharide.

It is a further specific object of the invention to provide a method of preventing bacterial meningitis in an animal comprising administering to the animal the meningococcal group B porin protein or fusion protein-vaccine produced according to the above-described methods.

It is another specific object of the invention to provide a method of preparing a polysaccharide conjugate comprising: obtaining the above-described meningococcal group B porin protein or fusion protein; obtaining a polysaccharide from a *Neisseria meningitidis* organism; and conjugating the meningococcal group B porin protein or fusion protein to the polysaccharide.

It is another specific object of the invention to provide a method of purifying the above-described meningococcal group B porin protein or fusion protein comprising: lysing the transformed E. coli to release the meningococcal group B porin protein or fusion protein as part of insoluble inclusion bodies; washing the inclusion bodies with a buffer to remove contaminating E. coli cellular proteins; resuspending and dissolving the inclusion bodies in an aqueous solution of a denaturant; diluting the resultant solution in a detergent: and purifying the solubilized meningococcal group B porin protein or fusion protein by gel filtration and ion exchange chromatography.

It is another specific object of the invention to provide a method of refolding the above-described meningococcal group B porin protein or fusion protein comprising: lysing the transformed E. coli to release the meningococcal group B porin protein or fusion protein as part of insoluble inclusion bodies; washing the inclusion bodies with a buffer to remove contaminating E. coli cellular proteins; resuspending and dissolving the inclusion bodies in an aqueous solution of a denaturant; diluting the resultant solution in a detergent; and purifying the solubilized meningococcal group B porin protein or fusion protein by gel filtration to give the refolded protein in the eluant.

It is another specific object of the invention to provide an E. coli strain BL21 (DE3)ΔompA host cell that contains a vector which comprises a DNA molecule coding for a meningococcal group B porin protein or fusion protein, wherein the DNA molecule is operably linked to the T7 promotor of the vector.

It is another specific object of the invention to provide the E coli strain BL21(DE3)ΔompA.

Further objects and advantages of the present invention will be clear from the description that follows.

BRIEF DESCRIPTION OF THE DRAWINGS

FIG. 4: The nucleotide sequence (SEQ ID NO. 1) and the translated amino acid sequence (SEQ ID NO. 2) of the mature PorB gene cloned into the expression plasmid pET-17b. The two nucleotides which differ from the previously published serotype 15 PorB are underlined.

FIGS. 9A and 9B: The nucleotide sequence (SEQ ID NO. 3) and the translated amino acid sequence (SEQ ID NO. 4) of the mature class II porin gene cloned into the expression plasmid pET-17b.

FIGS. 10A and 10B: The nucleotide sequence (SEQ ID NO. 5) and the translated amino acid sequence (SEQ ID NO. 6) of the fusion class II porin gene cloned into the expression plasmid pET-17b.

DETAILED DESCRIPTION OF THE INVENTION

Figure 1:
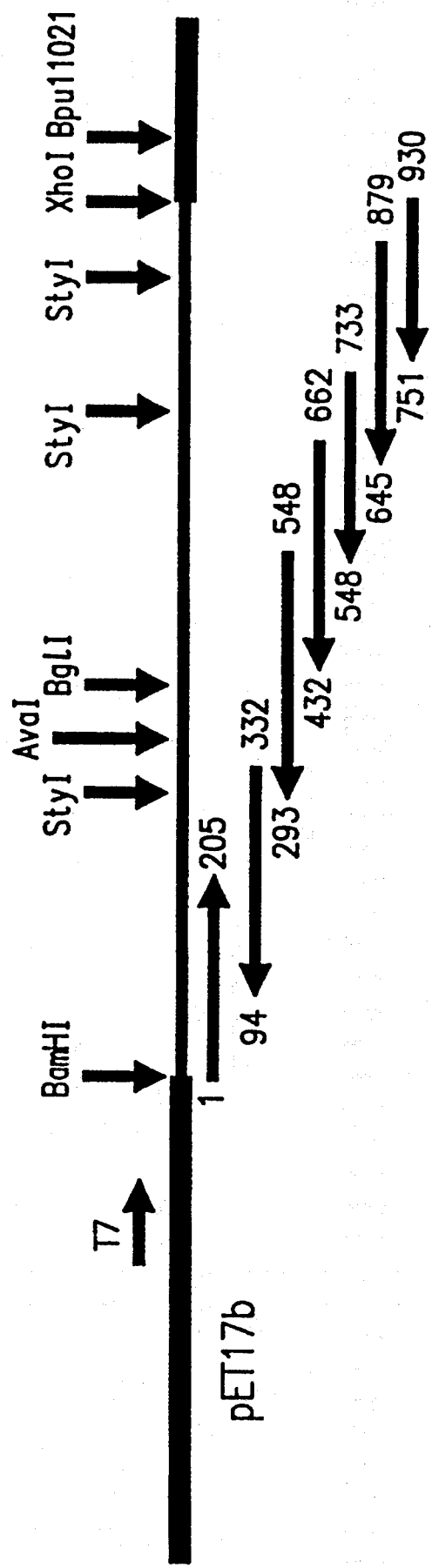
FIG. 1: A diagram showing the sequencing strategy of the PorB gene. The PCR product described in Example 1 (Materials and Methods section) was ligated into the BamHI-XhoI site of the expression plasmid pET-17b. The initial double stranded primer extension sequencing was accomplished using oligonucleotide sequences directly upstream of the BamHI site and just downstream of the XhoI site within the pET-17b plasmid. Additional sequence data was obtained by making numerous deletions in the 3' end of the gene, using exonuclease III/mung bean nuclease reactions. After religation and transformation back into E. coli, several clones were selected on size of insert and subsequently sequenced. This sequencing was always from the 3' end of the gene using an oligonucleotide primer just downstream of the Bpu1102I site.

Unlike the pore proteins of E. coli and a few other gram negative bacteria, relatively little is known how changes in the primary sequence of porins from Neisseria effect their ion selectivity, voltage dependence, and other biophysical functions. Recently, the crystalline structure of two E. coli porins, OmpF and PhoE, were solved to 2.4 Å and 3.0Å, respectively (Cowan, S. W., et al., *Nature* 358:727–733 (1992)). Both of these *E. coli* porins have been intensively studied owing to their unusual stability and ease with which molecular genetic manipulations could be accomplished. The data obtained for the genetics of these two porins correlated well with the crystalline structure. Although it has been shown in several studies, using monoclonal antibodies to select neisserial porins, that the surface topology of Neisseria closely resembles that of these two *E. coli* porins (van der Ley, P., et al., *Infect. Immun.* 59:2963–2971 (1991)), almost no information is available about how changes in amino acid sequences in specific areas of the neisserial porins effect their biophysical characteristics, as had been done with the *E. coli* porins (Cowan, S. W., et al., *Nature* 358:727–733 (1992)).

Two of the major problems impeding this research are: (1) the inability to easily manipulate Neisseria genetically by modern molecular techniques and (2) the inability to express sufficient quantities of neisserial porins in *E. coli* for further purification to obtain biophysical and biochemical characterization data. In fact, most of the DNA sequence data on gonococcal and meningococcal porins have been obtained by cloning overlapping pieces of the porin gene and then reconstructing the information to reveal the entire gene sequence (Gotschlich, E. C., et al., *Proc. Natl. Acad. Sci. USA* 84:8135–8139 (1987); Murakami, K., et al., *Infect. Immun.* 57:2318–2323 (1989)). Carbonetti et al. were the first to clone an entire gonococcal porin gene into *E. coli* using a tightly controlled pT7-5 expression plasmid. The results of these studies showed that when the porin gene was induced, very little porin protein accumulated and the expression of this protein was lethal to the *E. coli* (Carbonetti and Sparling, *Proc. Natl. Acad. Sci. USA* 84:9084–9088 (1987)). In additional studies, Carbonetti et al. (*Proc. Natl. Acad. Sci. USA* 85:6841–6845 (1988)) did show that alterations in the gonococcal porin gene could be made in this system in *E. coli* and then reintroduced into gonococci. However, the ease with which one can make these manipulations and obtain enough porin protein for further biochemical and biophysical characterization seems limited.

Feavers et al. have described a method to amplify, by PCR, neisserial porin genes from a wide variety of sources using two synthesized oligonucleotides to common domains at the 5' and 3' ends of the porin genes respectively (Feavers, I. M., et al., *Infect. Immun.* 60:3620–33629 (1992)). The oligonucleotides were constructed such that the amplified DNA could be forced cloned into plasmids using the restriction endonucleases BglII and XhoI.

Using the Feavers et al. PCR system, the DNA sequence of the mature PorB protein from meningococcal strain 8765 serotype 15 was amplified and ligated into the BamHI-XhoI site of the T7 expression plasmid pET-17b. This placed the mature PorB protein sequence in frame directly behind the T7 promoter and 20 amino acids of the φ10 protein including the leader sequence. Upon addition of IPTG to a culture of *E. coli* containing this plasmid, large amounts of PorB protein accumulated within the bacteria. A complete explanation for why this construction was non-lethal to the *E. coli* and expressed large amount of the porin protein, await further studies. However, one possible hypothesis is that by replacing the neisserial promoter and signal sequence with that of the T7 and φ10 respectively, the porin product was directed to the cytoplasm rather than toward the outer membrane. Henning and co-workers have reported that when *E. coli* OmpA protein and its fragments are expressed, those products which are found in the cytoplasm are less toxic than those directed toward the periplasmic space (Klose, M., et al., *J. Biol. Chem.* 263:13291–13296 (1988); Klose, M., et al., *J. Biol. Chem.* 263:13297–13302 (1988); Freudl, R., et al., *J. Mol. Biol.* 205:771–775 (1989)). Whatever the explanation, once the PorB protein was expressed, it was easily isolated, purified and appeared to reform into trimers much like the native porin. The results of the inhibition ELISA data using human immune sera suggests that the PorB protein obtained in this fashion regains most if not all of the antigenic characteristics of the wild type PorB protein purified from meningococci. This expression system lends itself to the easy manipulation of the neisserial porin gene by modern molecular techniques. In addition, this system allows one to obtain large quantities of pure porin protein for characterization. In addition, the present expression system allows the genes from numerous strains of Neisseria, both gonococci and meningococci, to be examined and characterized in a similar manner.

Thus, the present invention relates to a method of expressing an outer membrane meningococcal group B porin protein, in particular, the class 2 and class 3 porin proteins.

In one embodiment, the present invention relates to a method of expressing the outer membrane meningococcal group B porin protein in *E. coli* comprising:

(a) transforming *E. coli* by a vector comprising a selectable marker and a gene coding for a protein selected from the group consisting of:
  (i) a mature porin protein, and
  (ii) a fusion protein comprising a mature porin protein fused to amino acids 1 to 20 or 22 of the T7 gene φ10 capsid protein;

wherein said gene is operably linked to the T7 promoter;

(b) growing the transformed *E. coli* in a culture media containing a selection agent, and (c) inducing expression of said protein;

wherein the protein so produced comprises more than about 2% of the total protein expressed in the *E. coli*.

In a preferred embodiment, the meningococcal group B porin protein or fusion protein expressed comprises more than about 5% of the total proteins expressed in *E. coli*. In another preferred embodiment, the meningococcal group B porin protein or fusion protein expressed comprises more than about 10% of the total proteins expressed in *E. coli*. In yet another preferred embodiment, the meningococcal group B porin protein or fusion protein expressed comprises more than about 30% of the total proteins expressed in *E. coli*.

Examples of plasmids which contain the T7 inducible promotor include the expression plasmids pET-17b, pET-11a, pET-24a-d(+) and pET-9a, all of which are commercially available from Novagen (565 Science Drive, Madison, Wis. 53711). These plasmids comprise, in sequence, a T7 promoter, optionally a lac operator, a ribosome binding site, restriction sites to allow insertion of the structural gene and a T7 terminator sequence. See, the Novagen catalogue, pages 36–43 (1993).

In a preferred embodiment, *E. coli* strain BL21 (DE3)/ΔompA is employed. The above mentioned plasmids may be transformed into this strain or the wild-type strain BL21 (DE3). *E. coli* strain BL21 (DE3) ΔompA is preferred as no OmpA protein is produced by this strain which might contaminate the purified porin protein and create undesirable immunogenic side effects.

The transformed *E. coli* are grown in a medium containing a selection agent, e.g. any β-lactam to which *E. coli* is sensitive such as ampicillin. The pET expression vectors provide selectable markers which confer antibiotic resistance to the transformed organism.

High level expression of meningococcal group B porin protein can be toxic in *E. coli*. Surprisingly, the present invention allows *E. coli* to express the protein to a level of at least almost 30% and as high as >50% of the total cellular proteins.

In another preferred embodiment, the present invention relates to a vaccine comprising the outer membrane meningococcal group B porin protein or fusion protein thereof, produced according to the above-described methods, together with a pharmaceutically acceptable diluent, carrier, or excipient, wherein the vaccine may be administered in an amount effective to elicit protective antibodies in an animal to *Neisseria meningitidis*. In a preferred embodiment, the animal is selected from the group consisting of humans, cattle, pigs, sheep, and chickens. In another preferred embodiment, the animal is a human.

In another preferred embodiment, the present invention relates to the above-described vaccine, wherein said outer membrane meningococcal group B porin protein or fusion protein thereof is conjugated to a meningococcal group B capsular polysaccharide (CP). Such capsular polysaccharides may be prepared as described in Ashton, F. E. et al., *Microbial Pathog.* 6:455–458 (1989); Jennings, H. J. et al., *J. Immunol.* 134:2651 (1985); Jennings, H. J. et al., *J. Immunol.* 137:1708–1713 (1986); Jennings, H. J. et al., *J. Immunol.* 142:3585–3591 (1989); Jennings, H. J., "Capsular Polysaccharides as Vaccine Candidates," in *Current Topics in Microbiology and Immunology*, 150:105–107 (1990); the contents of each of which are fully incorporated by reference herein.

Preferably, the CP is isolated according to Frasch, C. E., "Production and Control of *Neisseria meningitidis* Vaccines" in *Bacterial Vaccines*, Alan R. Liss, Inc., pages 123–145 (1990), the contents of which are fully incorporated by reference herein, as follows:

Grow organisms in modified Franz medium 10 to 20 hrs
    Heat kill, 55° C., 10 min
    Remove inactivated cells by centrifugation
        Add Cetavlon to 0.1%
    Precipitate CP from culture broth
        Add calcium chloride to 1M
    Dissolve CP then centrifuge to remove cellular debris
        Add ethyl alcohol to 25%
    Remove precipitated nucleic acids by centrifugation
        Add ethyl alcohol to 80%
    Precipitate crude CP and remove alcohol The crude CP is then further purified by gel filtration chromatography after partial depolymerization with dilute acid, e.g. acetic acid, formic acid, and trifluoroacetic acid (0.01–0.5N), to give a mixture of polysaccharides having an average molecular weight of 12,000–16,000. The CP is then N-deacetylated with borohydride and N-propionylated to afford N—Pr GBMP. Thus, the CP that may be employed in the conjugate vaccines of the present invention may be CP fragments, N-deacylated CP and fragments thereof, as well as N—Pr CP and fragments thereof, so long as they induce active immunity when employed as part of a CP-porin protein conjugate (see the Examples).

In a further preferred embodiment, the present invention relates to a method of preparing a polysaccharide conjugate comprising: obtaining the above-described outer membrane meningococcal group B porin protein or fusion protein thereof; obtaining a CP from a *Neisseria meningitidis* organism; and conjugating the protein to the CP.

The conjugates of the invention may be formed by reacting the reducing end groups of the CP to primary amino groups of the porin by reductive amination. The reducing groups may be formed by selective hydrolysis or specific oxidative cleavage, or a combination of both. Preferably, the CP is conjugated to the porin protein by the method of Jennings et al., U.S. Pat. No. 4,356,170, the contents of which are fully incorporated by reference herein, which involves controlled oxidation of the CP with periodate followed by reductive amination with the porin protein.

The vaccine of the present invention comprises the meningococcal group B porin protein, fusion protein or conjugate vaccine in an mount effective depending on the route of administration. Although subcutaneous or intramuscular routes of administration are preferred, the meningococcal group B porin protein, fusion protein or vaccine of the present invention can also be administered by an intraperitoneal or intravenous route. One skilled in the art will appreciate that the mounts to be administered for any particular treatment protocol can be readily determined without undue experimentation. Suitable amounts might be expected to fall within the range of 2 micrograms of the protein per kg body weight to 100 micrograms per kg body weight.

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the meningococcal group B porin protein, fusion protein or conjugate vaccine have suitable solubility properties. The vaccines may be in the form of single dose preparations or in multi-dose flasks which can be used for mass vaccination programs. Reference is made to Remington's *Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

The meningococcal group B porin protein, fusion protein or conjugate vaccines of the present invention may further comprise adjuvants which enhance production of porin-specific antibodies. Such adjuvants include, but are not limited to, various oil formulations such as Freund's complete adjuvant (CFA), stearyl tyrosine (ST, see U.S. Pat. No. 4,258,029), the dipeptide known as MDP, saponin, aluminum hydroxide, and lymphatic cytokine.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) or ST may be used for administration to a human. The meningococcal group B porin protein or a conjugate vaccine thereof may be absorbed onto the aluminum hydroxide from which it is slowly released after injection. The meningococcal group B porin protein or conjugate vaccine may also be encapsulated within liposomes according to Fullerton, U.S. Pat. No. 4,235,877.

In another preferred embodiment, the present invention relates to a method of preventing bacterial meningitis in an animal comprising administering to the animal the meningococcal group B porin protein, fusion protein or conjugate vaccine produced according to methods described in an amount effective to prevent bacterial meningitis.

In a further embodiment, the invention relates to a method of purifying the above-described outer membrane meningococcal group B porin protein or fusion protein comprising: lysing the transformed *E. coli* to release the meningococcal group B porin protein or fusion protein as part of insoluble inclusion bodies; washing the inclusion bodies with a buffer to remove contaminating *E. coli* cellular proteins; resuspending and dissolving the inclusion bodies in an aqueous solution of a denaturant; diluting the resultant solution in a detergent; and purifying the solubilized meningococcal group B porin protein by gel filtration.

The lysing step may be carried out according to any method known to those of ordinary skill in the art, e.g. by sonication, enzyme digestion, osmotic shock, or by passing through a mull press.

The inclusion bodies may be washed with any buffer which is capable of solubilizing the *E. coli* cellular proteins without solubilizing the inclusion bodies comprising the meningococcal group B porin protein. Such buffers include but are not limited to TEN buffer (50 mM Tris HCl, 1 mM EDTA, 100 mM NaCl, pH 8.0), Tricine, Bicine and HEPES.

Denaturants which may be used in the practice of the invention include 2 to 8M urea or about 2 to 6M guanidine HCl, more preferably, 4 to 8M urea or about 4 to 6M guanidine HCl, and most preferably, about 8M urea or about 6M guanidine HCl).

Examples of detergents which can be used to dilute the solubilized meningococcal group B porin protein include, but are not limited to, ionic detergents such as SDS and cetavlon (Calbiochem); non-ionic detergents such as Tween, Triton X, Brij 35 and octyl glucoside; and zwitterionic detergents such as 3,14-Zwittergent, empigen BB and Champs.

Finally, the solubilized outer membrane meningococcal group B porin protein may be purified by gel filtration to separate the high and low molecular weight materials. Types of filtration gels include but are not limited to Sephacryl-300, Sepharose CL-6B, and Bio-Gel A-1.5 m. The column is eluted with the buffer used to dilute the solubilized protein. The fractions containing the porin or fusion thereof may then be identified by gel electrophoresis, the fractions pooled, dialyzed, and concentrated.

Finally, substantially pure (>95%) porin protein and fusion protein may be obtained by passing the concentrated fractions through a Q sepharose high performance column.

In another embodiment, the present invention relates to expression of the meningococcal group B porin protein gene which is part of a vector which comprises the T7 promoter, which is inducible. If a promoter is an inducible promoter, then the rate of transcription increases in response to an inducing agent. The T7 promoter is inducible by the addition of isopropyl β-D-thiogalactopyranoside (IPTG) to the culture medium.

Alternatively, the Tac promotor or heat shock promotor may be employed.

Preferably, the meningococcal group B porin protein gene is expressed from the pET-17 expression vector or the pET-11a expression vector, both of which contain the T7 promoter.

The cloning of the meningococcal group B porin protein gene or fusion gene into an expression vector may be carried out in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases. Reference is made to Sambrook et al., *Molecular Cloning: A Laboratory Manual*, 2nd ed., Cold Spring Harbor, N.Y., Cold Spring Harbor Laboratory Press (1989), for general methods of cloning.

The meningococcal group B porin protein and fusion protein expressed according to the present invention must be properly refolded in order to achieve a structure which is immunologically characteristic of the native protein. In yet another embodiment, the present invention relates to a method of refolding the above-described outer membrane protein and fusion protein comprising: lysing the transformed *E. coli* to release the meningococcal group B porin protein or fusion protein as part of insoluble inclusion bodies; washing the inclusion bodies with a buffer to remove contaminating *E. coli* cellular proteins; resuspending and dissolving the inclusion bodies in an aqueous solution of a denaturant; diluting the resultant solution in a detergent; and purifying the solubilized meningococcal group B porin protein or fusion protein by gel filtration to give the refolded protein in the eluant. Surprisingly, it has been discovered that the folded trimeric meningococcal group B class 2 and class 3 porin proteins and fusion proteins are obtained directly in the eluant from the gel filtration column.

In another preferred embodiment, the present invention relates to a substantially pure refolded outer membrane meningococcal group B porin protein and fusion protein produced according to the above-described methods. A substantially pure protein is a protein that is generally lacking in other cellular *Neisseria meningitidis* components as evidenced by, for example, electrophoresis. Such substantially pure proteins have a purity of >95%, as measured by densitometry on an electrophoretic gel after staining with Coomassie blue or silver stains.

The following examples are illustrative, but not limiting, of the method and compositions of the present invention. Other suitable modifications and adaptations of the variety of conditions and parameters normally encountered in this art which are obvious to those skilled in the art are within the spirit and scope of the present invention.

EXAMPLES

Example 1. Clotting of the Class 3 Porin Protein from Group B *Neisseria Meningitidis*

Materials and Methods

Organisms: The Group B *Neisseria meningitidis* strain 8765 (B:15:P1,3) was obtainer from Dr. Wendell Zollinger (Walter Reed Army Institute for Research) and grown on agar media previously described (Swanson, J. L., *Infect. Immun.* 21:292–302 (1978)) in a candle extinction jar in an incubator maintained at 30° C. *Escherichia* coli strains DME558 (from the collection of S. Benson; Silhavy, T. J. et al., "Experiments with Gene Fusions," Cold Spring Harbor Laboratory, Cold Spring Harbor, N.Y., 1984), BRE51 (Bremer, E. et al., *FEMS Microbiol. Lett.* 33:173–178 (1986)) and BL21(DE3) were grown on LB agar plates at 37° C.

P1Transduction: A P1$_{vir}$ lysate of *E. coli* strain DME558 was used to transduce a tetracycline resistance marker to strain BRE51 (Bremer, E., et al., *FEMS Microbiol. Lett.* 33:173–178 (1986)) in which the entire ompA gene had been deleted (Silhavy, T. J., et al., *Experiments with Gene Fusions*, Cold Spring Harbor Laboratory, Cold Spring Harbor, N.Y. (1984)). Strain DME558, containing the tetracycline resistance marker in close proximity of the ompA gene, was grown in LB medium until it reached a density of approximately 0.6 OD at 600 nm. One tenth of a milliliter of 0.5M CaCl$_2$ was added to the 10 ml culture and 0.1 ml of a solution containing $1 \times 10^9$ PFU of P1vir. The culture was incubated for 3 hours at 37° C. After this time, the bacterial cell density was visibly reduced. 0.5 ml of chloroform was added and the phage culture stored at 4° C. Because typically 1–2% of the *E. coli* chromosome can be packaged in each phage, the number of phage generated covers the entire bacterial host chromosome, including the tetracycline resistance marker close to the ompA gene.

Next, strain BRE51, which lacks the ompA gene, was grown in LB medium overnight at 37° C. The overnight culture was diluted 1:50 into fresh LB and grown for 2 hr. The cells were removed by centrifugation and resuspended in MC salts. 0.1 ml of the bacterial cells were mixed with 0.05 of the phage lysate described above and incubated for 20 min. at room temperature. Thereafter, an equal volume of 1M sodium citrate was added and the bacterial cells were plated out onto LB plates containing 12.5 μg/ml of tetracycline. The plates were incubated overnight at 37° C. Tetracycline resistant (12 μg/ml) transductants were screened for lack of OmpA protein expression by SDS-PAGE and Western Blot analysis, as described below. The bacteria resistant to the antibiotic have the tetracycline resistance gene integrated into the chromosome very near where the ompA gene had been deleted from this strain. One particular strain was designated BRE-T®.

A second round of phage production was then carried out with the strain BRE-T®, using the same method as described above. Representatives of this phage population contain both the tetracycline resistance gene and the OmpA deletion. These phage were then collected and stored. These phage were then used to infect *E. coli* BL21(DE3). After infection, the bacteria contain the tetracycline resistance marker. In addition, there is a high probability that the OmpA deletion was selected on the LB plates containing tetracycline.

Colonies of bacteria which grew on the plates were grown up separately in LB medium and tested for the presence of the OmpA protein. Of those colonies selected for examination, all lacked the OmpA protein as judged by antibody reactivity on SDS-PAGE western blots.

SDS-PAGE and Western Blot: The SDS-PAGE was a variation of Laemmli's method (Laemmli, U. K., *Nature* 227:680–685 (1970)) as described previously (Blake and Gotschlich, *J. Exp. Med.* 159:452–462 (1984)). Electrophoretic transfer to Immobilon P (Millipore Corp. Bedford, Mass.) was performed according to the methods of Towbin et al. (Towbin, H., et al., *Proc. Natl. Acad. Sci.* USA 76:4350–4354 (1979)) with the exception that the paper was first wetted in methanol. The Western blots were probed with phosphatase conjugated reagents (Blake, M. S., et al., *Analyt. Biochem.* 136:175–179 (1984)).

Polymerase Chain Reaction: The method described by Feavers et al. (Feavers, I. M., et al., *Infect. Immun.* 60:3620–3629 (1992)) was used to amplify the gene encoding the PorB. The primers selected were primers 33 (SEQ ID NO. 11)(GGG GTA GAT CTG CAG GTT ACC TTG TAG GGT ACA ATT AAA GCA GGC GT) and 34 (SEQ ID NO. 12) (GGG GGG GTG ACC CTC GAG TTA GAA TTT GTG ACG CAG ACC AAC) as previously described (Feavers, I. M., et al., *Infect. Immun.* 60:3620–3629 (1992)). Briefly, the reaction components were as follows: Meningococcal strain 8765 chromosomal DNA (100 ng/μl), 1 μl; 5' and 3' primers (1μM) 2 μl each; dNTP (10 mM stocks), 4 μl each; 10×PCR reaction buffer (100 mM Tris HCl, 500 mM KCl, pH 8.3), 10 μl; 25 mM MgCl$_2$, 6 μl; double distilled H$_2$O, 62 μl; and Taq polymerase (Cetus Corp., 5 u/μl), 1 μl. The reaction was carried out in a GTC-2 Genetic Thermocycler (Precision Inst. Inc, Chicago, Ill.) connected to a Lauda 4/K methanol/water cooling system (Brinkman Instruments, Inc., Westbury, N.Y.) set at 0° C. The thermocycler was programmed to cycle 30 times through: 94° C., 2 min.; 40° C., 2 min.; and 72° C., 3 min. At the end of these 30 cycles, the reaction was extended at 72° C. for 3 min and finally held at 4° C. until readied for analysis on a 1% agarose gel in TAE buffer as described by Maniatis (Maniatis, T., et al., *Molecular Cloning, A Laboratory Manual*, Cold Spring Harbor Laboratory, Cold Spring Harbor, N.Y. (1982)).

Subcloning of the PCR product: The pET-17b plasmid (Novagen, Inc.) was used for subcloning and was prepared by double digesting the plasmid with the restriction endonucleases BamHI and XhoI (New England Biolabs, Inc., Beverly, Mass.). The digested ends were then dephosphorylated with calf intestinal alkaline phosphatase (Boehringer Mannheim, Indianapolis, Ind.). The digested plasmid was then analyzed on a 1% agarose gel, the cut plasmid removed, and purified using the GeneClean kit (Bio101, La Jolla, Calif.). The PCR product was prepared by extraction with phenol-chloroform, chloroform, and finally purified using the GeneClean Kit (Bio101). The PCR product was digested with restriction endonucleases BglII and XhoI (New England Biolabs, Inc.). The DNA was then extracted with phenol-chloroform, precipitated by adding 0.1 volumes of 3M sodium acetate, 5 μl glycogen (20 μg/μl), and 2.5 volumes of ethanol. After washing the DNA with 70% ethanol (vol/vol), it was redissolved in TE buffer. The digested PCR product was ligated to the double digested pET-17b plasmid described above using the standard T4 ligase procedure at 16° C. overnight (*Current Protocols in Molecular Biology*, John Wiley & Sons, N.Y. (1993)). The ligation product was then transformed into the BL21 (DE3)-ΔompA described above which were made competent by the method of Chung et al. (Chung, C. T., et al., *Proc. Natl. Acad. Sci.* USA 86:2172–2175 (1989)). The transformants were selected on LB plates containing 50 μg/ml carbenicillin yard 12 μg/ml tetracycline. Several transformants were selected, cultured in LB both containing carbenicillin and tetracycline for 6 hours at 30° C., and plasmid gene expression inducted by the addition of IPTG. The temperature was raised to 37° C. and the cultures continued for an additional 2 hrs. The cells of each culture were collected by centrifugation, whole cell lysates prepared, and analyzed by SDS-PAGE and Western Blot using a monoclonal antibody (4D11) which reacts with all neisserial porins.

Nucleotide Sequence Analysis: The nucleotide sequences of the cloned Class 3 porin gene DNA were determined by the dideoxy method using denatured double-stranded plasmid DNA as the template as described (*Current Protocols in Molecular Biology*, John Wiley & Sons, New York (1993)). Sequenase II kits (United States Biochemical Corp., Cleveland, Ohio) were used in accordance with the manufacturer's instructions. The three synthesized oligonucleotide primers (Operon Technologies, Inc., Alameda, Calif.) were used for these reactions. One for the 5' end(SEQ ID NO. 13) which consisted of 5'TCAAGCTTGGTACC-GAGCTC and two for the 3' end, (SEQ ID NO. 14) 5'TTTGTTAGCAGCCGGATCTG (SEQ ID NO. 15) and 5' CTCAAGACCCGTTTAGAGGCC. Overlapping, nested deletions were made by linearizing the plasmid DNA by restriction endonuclease Bpu11021 and the ends blunted by the addition of Thio-dNTP and Klenow polymerase (*Current Protocols in Molecular Biology*, John Wiley & Sons, New York (1993)). The linearized plasmid was then cleaved with restriction endonuclease XhoI and the exoII/Mung bean nuclease deletion kit used to make 3' deletions of the plasmid (Stratagene, Inc., La Jolla, Calif.) as instructed by the supplier. A map of this strategy is shown in FIG. 1.

Expression and purification of the PorB gene product: Using a sterile micropipette tip, a single colony of the BL21 (DE3)-ΔompA containing the PorB-pET-17b plasmid was selected and inoculated into 10 ml of LB broth containing 50 μg/ml carbenicillin. The culture was incubated overnight at 30° C. while shaking. The 10 ml overnight culture was then sterily added to 1 liter of LB broth with the same concentration of carbenicillin, and the culture continued in a shaking incubator at 37° C. until the $OD_{600}$ reached 0.6–1.0. Three mls of a stock solution of IPTG (100 mM) was added to the culture and the culture incubated for an additional 30 min. Rifampicin was then added (5.88 ml of a stock solution; 34 mg/ml in methanol) and the culture continued for an additional 2 hrs. The cells were harvested by centrifugation at 10,000 rpm in a GS3 rotor for 10 min and weighed. The cells were thoroughly resuspended in 3 ml of TEN buffer (50 mM Tris HCl, 1 mM Tris HCl, 1 mM EDTA, 100 mM NaCl, pH 8.0) per gram wet weight of cells. To this was added 8 μl of PMSF stock solution (50 mM in anhydrous ethanol) and 80 μl of a lysozyme stock solution (10 mg/ml in water) per gram wet weight of cells. This mixture was stirred at room temperature for 20 min. While stirring, 4 mg per gram wet weight of cells of deoxycholate was added. The mixture was placed in a 37° C. water bath and stirred with a glass rod. When the mixture became viscous, 20 μl of DNase I stock solution (1 mg/ml) was added per gram weight wet cells. The mixture was then removed from the water bath and left at room temperature until the solution was no longer viscous. The mixture was then centrifuged at 15,000 rpm in a SS-34 rotor for 20 min at 4° C. The pellet was retained and thoroughly washed twice with TEN buffer. The pellet was then resuspended in freshly prepared TEN buffer containing 0.1 mM PMSF and 8M urea and sonicated in a bath sonicator (Heat Systems, inc., Plainview, N.Y.). The protein concentration was determined using a BCA kit (Pierce, Rockville, Ill.) and the protein concentration adjusted to less than 10 mg/ml using the TEN-urea buffer. The sample was then diluted 1:1 with 10% (weight/vol) Zwittergent 3,14 (CalBiochem, La Jolla, Calif.), sonicated, and loaded onto a Sephacryl S-300 molecular sieve column. The Sephacryl S-300 column (2.5 cm×200 cm) had previously equilibrated with 100 mM Tris HCl, 200 mM NaCl, 10 mM EDTA, 0.05% Zwittergent 3,14, and 0.02% azide, pH 8.0. The column flow rate was adjusted to 8 ml/hr and 10 ml fractions were collected. The $OD_{280}$ of each fraction was measured and SDS-PAGE analysis performed on protein containing fractions.

Inhibition ELISA Assays: Microtiter plates (Nunc-Immuno Plate IIF, Nunc, Inc., Naperville, Ill.) were sensitized by adding 0.1 ml per well of porB (2 μg/ml) purified from the wild type strain 8765, in 0.1M carbonate buffer, pH 9.6 with 0.02% azide. The plates were incubated overnight at room temperature. The plates were washed five times with 0.9% NaCl, 0.05% Brij 35, 10 mM sodium acetate pH 7.0, 0.02% azide. Human immune sera raised against the Type 15 Class 3 PorB protein was obtained from Dr. Phillip O. Livingston, Memorial-Sloan Kettering Cancer Center, New York, N.Y. The human immune sera was diluted in PBS with 0.5% Brij 35 and added to the plate and incubated for 2 hr at room temperature. The plates were again washed as before and the secondary antibody, alkaline phosphatase conjugated goat anti-human IgG (Tago Inc., Burlingame, Calif.), was diluted in PBS-Brij, added to the plates and incubated for 1 hr at room temperature. The plates were washed as before and p-nitrophenyl phosphate (Sigma Phosphatase Substrate 104) (1 mg/ml) in 0.1 diethanolamine, 1 mM $MgCl_2$, 0.1 mM $ZnCl_2$, 0.02% azide, pH 9.8, was added. The plates were incubated at 37° C. for 1 h and the absorbance at 405 nm determined using an Elida-5 microtiter plate reader (Physica, New York, N.Y.). Control wells lacked either the primary and/or secondary antibody. This was done to obtain a titer for each human serum which would give a half-maximal reading in the ELISA assay. This titer for each human serum would be used in the inhibition ELISA. The ELISA microtiter plate would be sensitized with purified wild type PorB protein and washed as before. In a separate V-96 polypropylene microtiter plate (Nunc, Inc.), varying amounts of either purified wild type PorB protein or the purified recombinant PorB protein were added in a total volume of 75 μl. The human sera were diluted in PBS-Brij solution to twice their half maximal titer and 75 μl added to each of the wells containing the PorB or recombinant PorB proteins. This plate was incubated for 2 hr at room temperature and centrifuged in a Sorvall RT6000 refrigerated centrifuge, equipped with microtiter plate carriers (Wilmington, Del.) at 3000 rpm for 10 min. Avoiding the V-bottom, 100 μl from each well was removed and transferred to the sensitized and washed ELISA microtiter plate. The ELISA plates are incubated for an additional 2 hr, washed, and the conjugated second antibody added as before. The plate is then processed and read as described. The percentage of inhibition is then processed and read as described. The percentage of inhibition is calculated as follows:

$$1 - \frac{\text{(ELISA value with either PorB or rPorB protein added)}}{\text{(ELSIA value without the porB added)}} \times 100$$

Results

Figure 2:
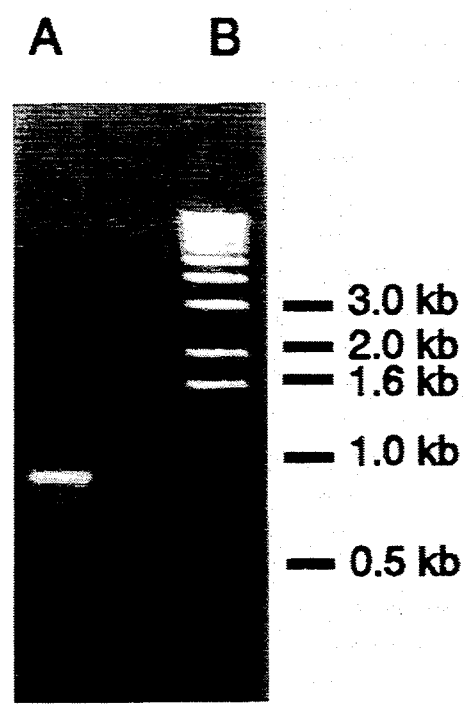
FIG. 2: A gel electrophoresis showing the products of the PCR reaction (electrophoresed in a 1% agarose using TAE buffer).

Polymerase Chain Reaction and Subcloning: A method to easily clone, genetically manipulate, and eventually obtain enough pure porin protein from any number of different neisserial porin genes for further antigenic and biophysical characterization has been developed. The first step toward this goal was cloning the porin gene from a Neisseria. Using a technique originally described by Feavers, et al. (Feavers, I. M., et al., *Infect. Immun.* 60:3620-3629 (1992)), the DNA sequence of the mature porin protein from a class 3, serotype 15 porin was amplified using the chromosome of meningococcal strain 8765 as a template for the PCR reaction. Appropriate endonuclease restriction sites had been synthesized onto the ends of the oligonucleotide primers, such that when cleaved, the amplified mature porin sequence could be directly ligated and cloned into the chosen expression plasmid. After 30 cycles, the PCR products shown in FIG. 2 were obtained. The major product migrated between 900 bp and 1000 bp which was in accord with the previous study (Feavers, I. M., et al., *Infect. Immun.* 60:3620-3629 (1992)). However, a higher molecular weight product was not seen, even though the PCR was conducted under low annealing stringencies (40° C.; 50 mM KCl).

Figure 3A:
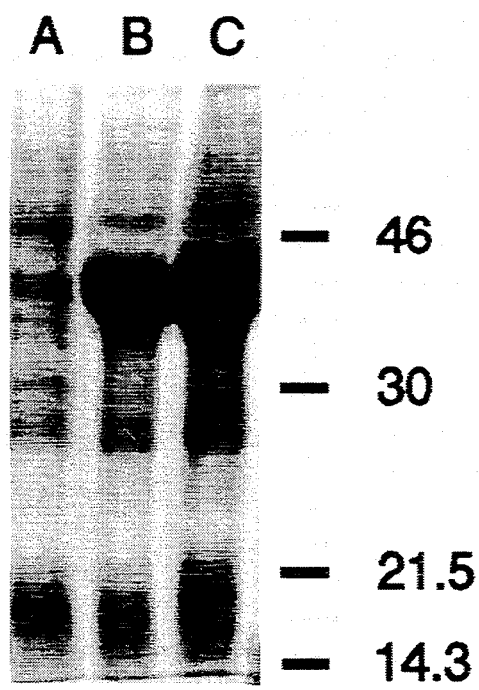
FIG. 3 (panels (a) and (b)). Panel (a): SDS-PAGE analysis of whole cell lysates of E. coli hosting the control pET-17b plasmid without inserts and an E. coli clone harboring pET-17b plasmid containing an insert from the obtained PCR product described in the materials and methods section. Both cultures were grown to an O.D. of 0.6 at 600 nm, IPTG added, and incubated at 37° C. for 2 hrs. 1.5 mls of each of the cultures were removed, centrifuged, and the bacterial pellet solubilized in 100 μl of SDS-PAGE preparation buffer. Lane A shows the protein profile obtained with 10 μl from the control sample and Lanes B (5 μl) and C (10 μl) demonstrate the protein profile of the E. coli host expressing the PorB protein. Panel (b): Western blot analysis of whole cell lysates of E. coli harboring the control pET-17b plasmid without insert after 2 hrs induction with IPTG, Lane A, 20 μl and a corresponding E. coli clone containing a porB-pET-17b plasmid, Lane B, 5 μl; Lane C, 10 μl; and Lane D, 20 μl. The monoclonal antibody 4D11 was used as the primary antibody and the western blot developed as described. The prestained low molecular weight standards from BRL were used in each case.
Figure 3B:
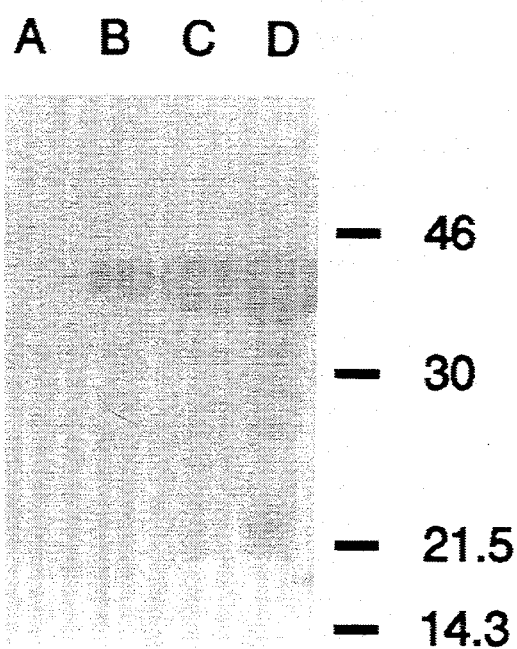

To be able to produce large amounts of the cloned porin protein, the tightly controlled expression system of Studier, et al. (Studier and Moffatt, *J. Mol. Biol.* 189:113-130 (1986)) was employed, which is commercially available through Novagen Inc. The amplified PCR product was cloned into the BamHI-XhoI site of plasmid pET-17b. This strategy places the DNA sequence for the mature porin protein in frame directly behind the T7 promoter, the DNA sequence encoding for the 9 amino acid leader sequence and 11 amino acids of the mature $\phi$10 protein. The Studier *E. coli* strain BL21 lysogenic for the DE3 lambda derivative (Studier and Moffatt, *J. Mol. Biol.* 189:113-130 (1986)) was selected as the expression host for the pET-17b plasmid containing the porin gene. But because it was thought that the OmpA protein, originating from the *E. coli* expression host, might tend to co-purify with the expressed meningococcal porin protein, a modification of this strain was made by P1 transduction which eliminated the ompA gene from this strain. Thus, after restriction endonuclease digestion of both the PCR product and the pET-17b vector and ligation, the product was transformed into BL21(DE3)-$\Delta$ompA and transformants selected for ampicillin and tetracycline resistance. Of the numerous colonies observed on the selection plate, 10 were picked for further characterization. All ten expressed large amounts of a protein, which migrated at the approximate molecular weight of the PorB protein, when grown to log phase and induced with IPTG. The whole cell lysate of one such culture is shown in FIG. 3a. The western blot analysis with the 4D11 monoclonal antibody further suggested that the protein being expressed was the PorB protein (FIG. 3b). As opposed to other studies, when neisserial porins have been cloned and expressed in *E. coli*, the host bacterial cells showed no signs of any toxic or lethal effects even after the addition of the IPTG. The *E. coli* cells appeared viable and could be recultured at any time throughout the expression phase.

Nucleotide sequence analysis: The amount of PorB expressed in these experiments was significantly greater than that previously observed and there appeared to be no adverse effects of this expression on the host *E. coli*. To be certain that no PCR artifacts had been introduced into the meningococcal porin gene to allow for such high expression, the entire $\phi$10 porin fusion was sequenced by double stranded primer extension from the plasmid. The results are shown in FIG. 4. The nucleotide sequence was identical with another meningococcal serotype 15 PorB gene sequence previously reported by Heckels, et al. (Ward, M. J., et al., *FEMS Microbiol. Lett.* 73:283-289 (1992)) with two exceptions which are shown. These two nucleotide differences each occur in the third position of the codon and would not alter the amino acid sequence of the expressed protein. Thus, from the nucleotide sequence, there did not appear to be any PCR artifact or mutation which might account for the high protein expression and lack of toxicity within the *E. coli*. Furthermore, this data would suggest that a true PorB protein was being produced.

Figure 5:
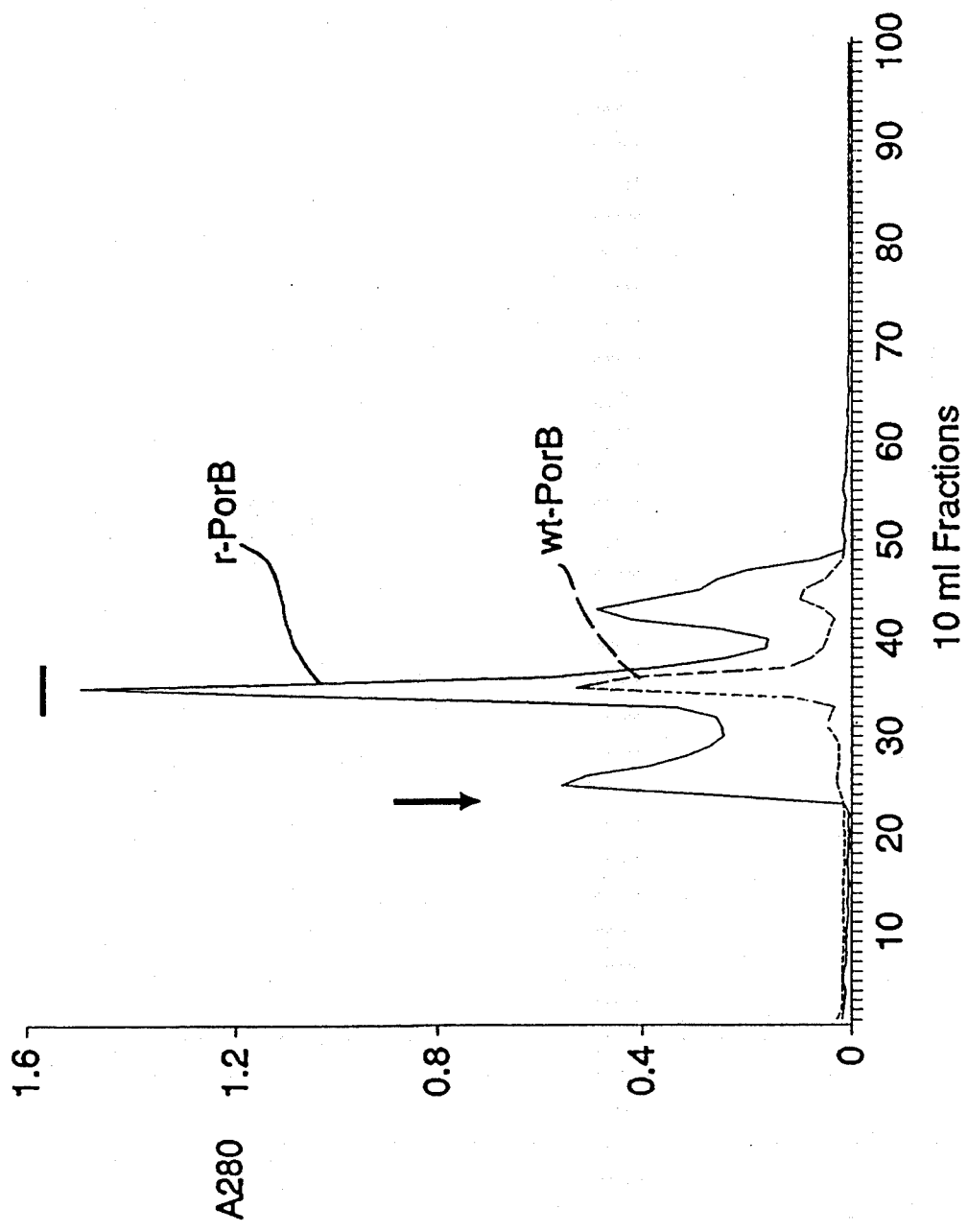
FIG. 5: A graph showing the Sephacryl S-300 column elution profile of both the wild type Class 3 protein isolated from the meningococcal strain 8765 and the recombinant Class 3 protein produced by BL21 (DE3)-ΔompA E. coli strain hosting the r3pET-17b plasmid as monitored by absorption at 280 nm and SDS-PAGE analysis. The void volume of the column is indicated by the arrow. Fractions containing the meningococcal porin and recombinant porin as determined by SDS-PAGE are noted by the bar.

Purification of the expressed porB gene product: The PorB protein expressed in the *E. coli* was insoluble in TEN buffer which suggested that when expressed, the PorB protein formed into inclusion bodies. However, washing of the insoluble PorB protein with TEN buffer removed most of the contaminating *E. coli* proteins. The PorB protein could then be solubilized in freshly prepared 8M urea and diluted into the Zwittergent 3,14 detergent. The final purification was accomplished, using a Sephacryl S-300 molecular sieve column which not only removed the urea but also the remaining contaminating proteins. The majority of the PorB protein eluted from the column having the apparent molecular weight of trimers much like the wild type PorB. The comparative elution patterns of both the wild type and the PorB expressed in the *E. coli* are shown in FIG. 5. It is important to note that when the PorB protein concentration in the 8M urea was in excess of 10 mg/ml prior to dilution into the Zwittergent detergent, the relative amounts of PorB protein found as trimers decreased and appeared as aggregates eluting at the void volume. However, at protein concentrations below 10 mg/ml in the urea buffer, the majority of the PorB eluted in the exact stone fraction as did the wild type PorB. It was also determined using a T7 -Tag monoclonal antibody and western blot analysis that the 11 amino acids of the mature T7 capsid protein were retained as the amino terminus. The total yield of the meningococcal porin protein from one liter of *E. coli* was approximately 50 mg.

Figure 6:
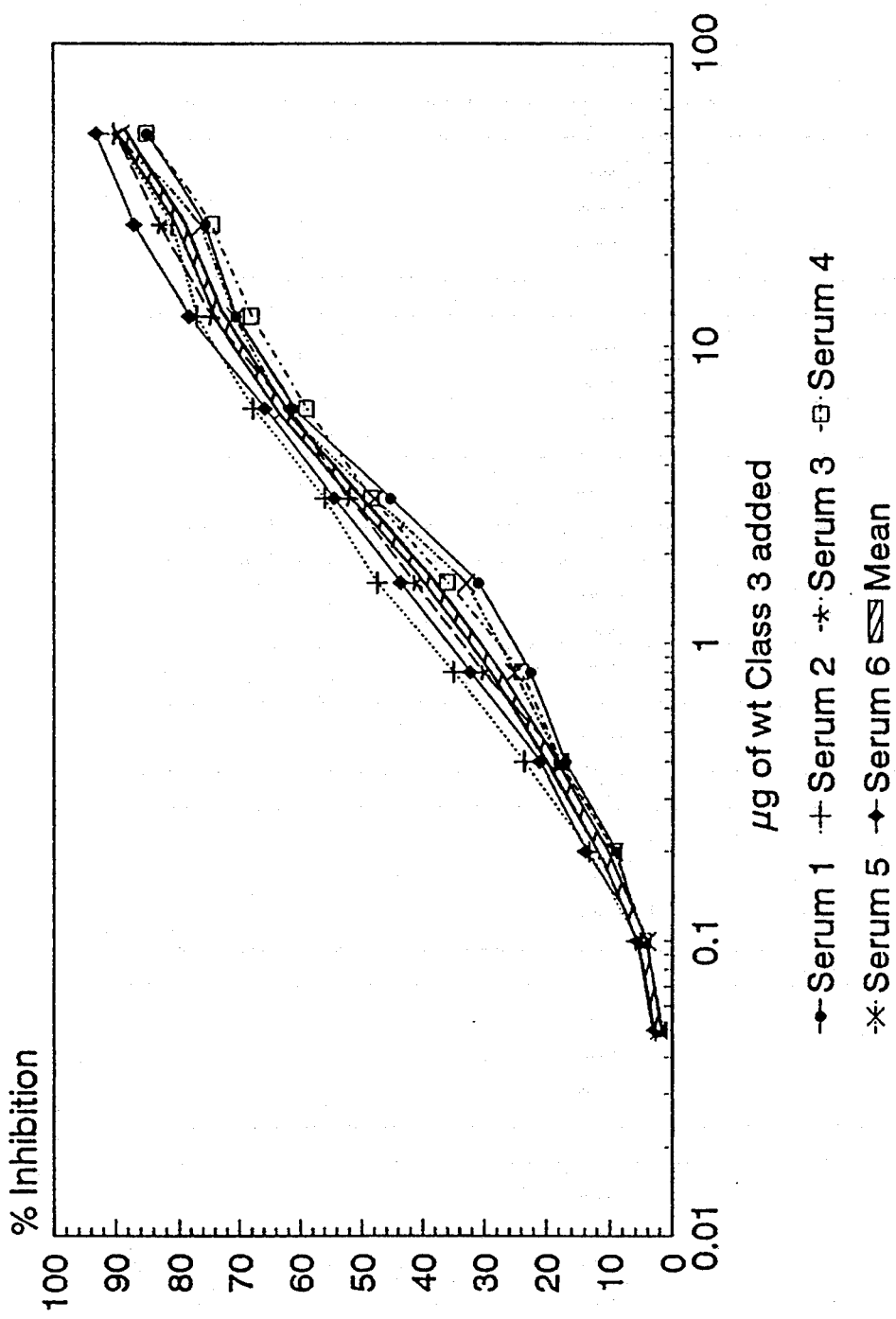
FIG. 6: A graph showing the results of the inhibition ELISA assays showing the ability of the homologous wild type (wt) PorB to compete for reactive antibodies in six human immune sera. The arithmetic mean inhibition is shown by the bold line.
Figure 7:
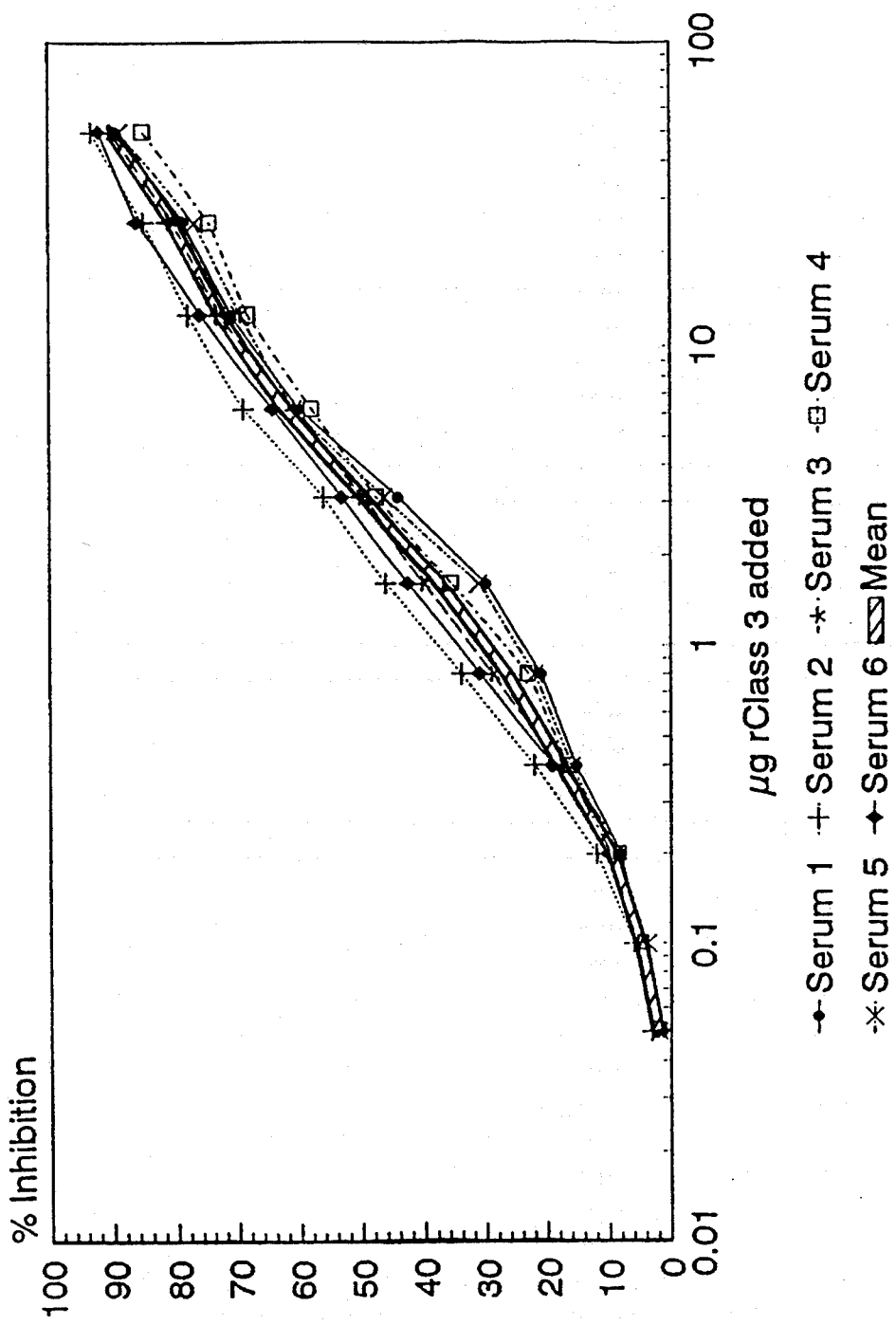
FIG. 7: A graph showing the results of the inhibition ELISA assays showing the ability of the purified recombinant PorB protein to compete for reactive antibodies in six human immune sera. The arithmetic mean inhibition is shown by the bold fine.
Figure 8:
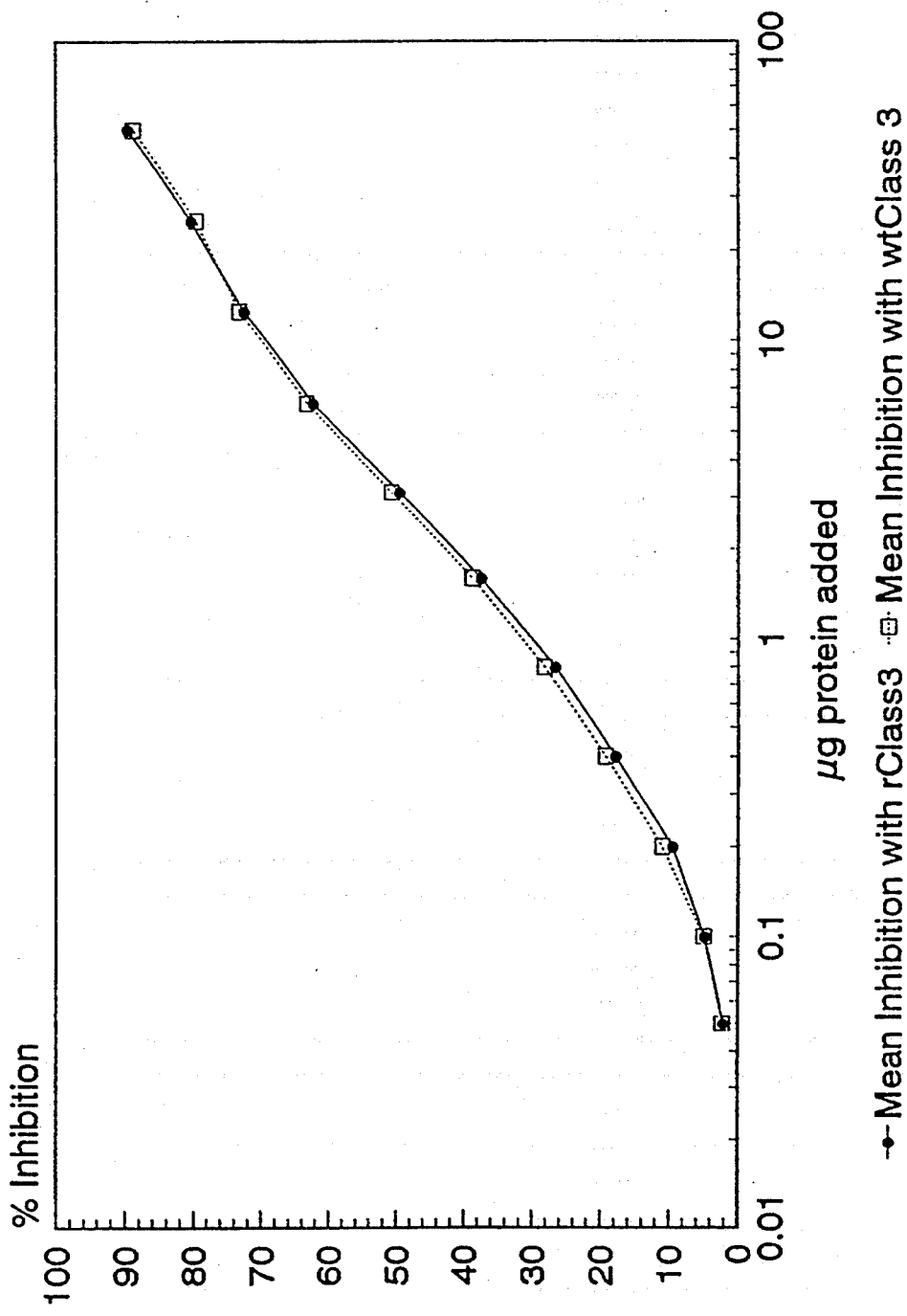
FIG. 8: A graph showing a comparison of these two mean inhibitions obtained with the wt and recombinant PorB protein.
Figure 11A:
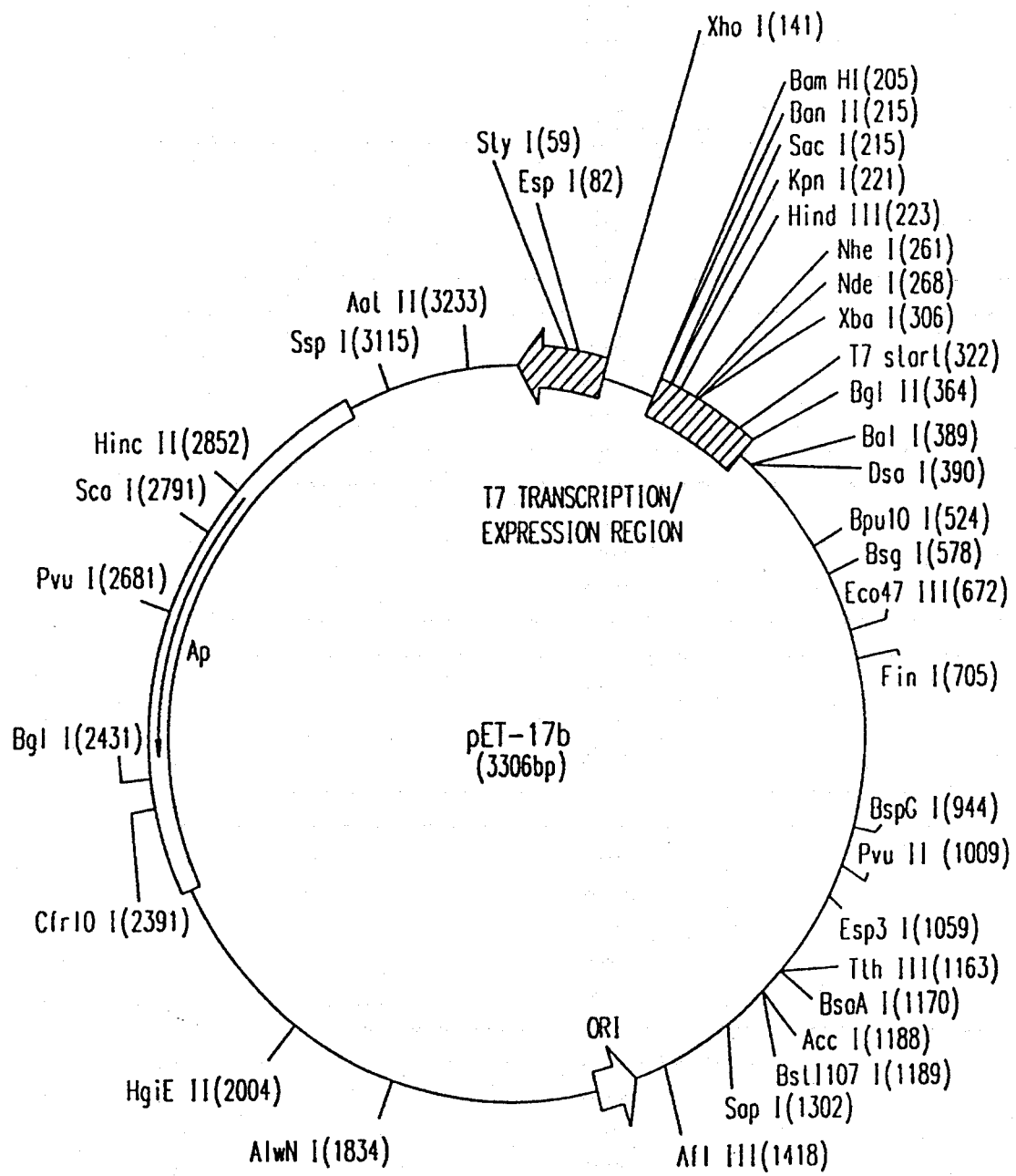
FIG. 11 (panels A and B): Panel A depicts the restriction map of the pET-17b plasmid. Panel B depicts the nucleotide sequence (SEQ ID NO. 7 AND SEQ ID NO. 9) between the BglII and XhoI sites of pET-17b. The sequence provided by the plasmid is in normal print while the sequence inserted from the PCR product are identified in bold print. The amino acids (SEQ ID NO. 8 AND SEQ ID NO. 10) which are derived from the plasmid are in normal print while the amino acids from the insert are in bold. The arrows demarcate where the sequence begins to match the sequence in FIG. 4 and when it ends.

Inhibition ELISA Assays. In order to determine if the purified trimeric recombinant PorB had a similar antigenic conformation as compared to the PorB produced in the wild type meningococcal strain 8765, the sera from six patients which had been vaccinated with the wild type meningococcal Type 15 PorB protein were used in inhibition ELISA assays. In the inhibition assay, antibodies reactive to the native PorB were competitively inhibited with various amounts of either the purified recombinant PorB or the homologous purified wild type PorB. The results of the inhibition with the homologous purified PorB of each of the six human sera and the mean inhibition of these sera are shown in FIG. 6. The corresponding inhibition of these sera with the purified recombinant PorB is seen in FIG. 6b. A comparison of the mean inhibition from FIGS. 6 and 7 are plotted in FIG. 8. These data would suggest that the antibodies contained in the sera of these six patients found similar epitopes on both the homologous purified wild type PorB and the purified recombinant PorB.

This gave further evidence that the recombinant PorB had regained most if not all of the native conformation found in the wild type PorB.

Example 2. Cloning of the Class 2 Porin from Group B Neisseria Meningitidis strain BNCV M986

Genomic DNA was isolated from approximately 0.5 g of Group B *Neisseria meningitidis* strain BNCV M986 (serotype 2a) using previously described methods (Sambrook et al., *Molecular Cloning: A Laboratory Manual,* 2nd ed., Cold Spring Harbor, N.Y., Cold Spring Harbor Laboratory Press (1989)). This DNA then served as the template for two class 2 porin specific oligonucleotides in a standard PCR reaction. These oligonucleotides were designed to be complementary to the 5' and 3' flanking regions of the class 2 porin and to contain EcoRI restriction sites to facilitate the cloning of the fragment. The sequences of the oligonucleotides were as follows: (SEQ ID NO. 16) 5' AGC GGC TTG GAA TTC CCG GCT GGC TTA AAT TTC 3' (SEQ ID NO. 17) and 5' CAA ACG AAT GAA ITC AAA TAA AAA AGC CTG 3'. The polymerase chain reaction was then utilized to obtain the class 2 porin. The reaction conditions were as follows: BNCV M986 genomic DNA 200 ng, the two oligonucleotide primers described above at 1 μM of each, 200 μM of each dNTP, PCR reaction buffer (10 mM Tris HCl, 50 mM KCl, pH 8.3), 1.5 mM $MgCl_2$, and 2.5 units of Taq polymerase, made up to 100 μl with distilled $H_2O$. This reaction mixture was then subjected to 25 cycles of 95° C. for 1 min, 50° C. for 2 min and 72° C. for 1.5 min. At the end of the cycling period, the reaction mixture was loaded on a 1% agarose gel and the material was electrophoresed for 2 h after which the band at 1.3 kb was removed and the DNA recovered using the Gene Clean kit (Bio 101). This DNA was then digested with EcoRI, repurified and ligated to EcoRI digested pUC19 using $T_4$ DNA ligase. The ligation mixture was used to transform competent *E. coli* DH5α. Recombinant plasmids were selected and sequenced. The insert was found to have a DNA sequence consistent with that of a class 2 pore. See, Murakami, K. et al., *Infect. Immun.* 57:2318–2323 (1989).

The plasmid pET-17b (Novagen) was used to express the class 2 porin. As described below, two plasmids were constructed that yielded two different proteins. One plasmid was designed to produce a mature class 2 porin while the other was designed to yield a class 2 porin fused to 20 amino acids from the T7 gene φ10 capsid protein.

Construction of the Mature Class 2 Porin

The mature class 2 porin was constructed by amplifying the pUC19-class 2 porin construct using the oligonucleotides (SEQ ID NO. 18) 5' CCT GTT GCA GCA CAT ATG GAC GTT ACC TTG TAC GGT ACA ATT AAA GC 3' and (SEQ ID NO. 19) 5' CGA CAG GCT TTT TCT CGA GAC CAA TCT TTT CAG 3'. This strategy allowed the cloning of the amplified class 2 porin into the Ndel and Xhol sites of the plasmid pET-17b thus producing a mature class 2 porin. Standard PCR was conducted using the pUC19-class 2 as the template and the two oligonucleotides described above. This PCR reaction yielded a 1.1 kb product when analyzed on a 1.0% agarose gel. The DNA obtained from the PCR reaction was gel purified and digested with the restriction enzymes Ndel and Xhol. The 1.1 kb DNA produced was again gel purified and ligated to Ndel and Xhol digested pET-17b using $T_4$ DNA ligase. This ligation mixture was then used to transform competent *E. coli* DH5α. Colonies that contained the 1.1 kb insert were chosen for further analysis. The DNA from the DH5α clones was analyzed by restriction mapping and the cloning junctions of the chosen plasmids were sequenced. After this analysis, the DNA obtained from the DH5α clones was used to transform *E. coli* BL21(DE3)-ΔompA. The transformants were selected to LB-agar containing 100 μg/ml of carbenicillin. Several transformants were screened for their ability to make the class 2 porin protein. This was done by growing the clones in LB liquid medium containing 100 μg/ml of carbenicillin and 0.4% glucose at 30° C. to $OD_{600}$=0.6 then inducing the cultures with IPTG (0.4 mM). The cells were then disrupted and the cell extract was analyzed by SDS-PAGE.

Construction of the Fusion Class 2 Porin

The fusion class 2 porin was constructed by amplifying the pUC19-class 2 porin construct using the oligonucleotides (SEQ ID NO. 20) 5' CCT GTT GCA GCG GAT CCA GAC GTT ACC TTG TAC GGT ACA ATT AAA GC 3' and (SEQ ID NO. 21) 5' CGA CAG GCT TTT TCT CGA GAC CAA TCT TTT CAG 3'. This strategy allowed the cloning of the amplified class 2 porin into the BamHI and XhoI sites of the plasmid pET-17b thus producing a fusion class 2 porin containing an additional 22 amino acids at the N-tetanus derived from the T7 φ10 capsid protein contained in the plasmid. Standard PCR was conducted using the pUC19-class 2 as the template and the two oligonucleotides described above. The PCR reaction yielded a 1.1 kb product when analyzed on a 1.0% agarose gel. The DNA obtained from the PCR reaction was gel purified and digested with the reaction enzymes BamHI and XhoI. The 1.1 kb product produced was again gel purified and ligated to BamHI and XhoI digested pET-17b using $T_4$ DNA ligase. This ligation mixture was then used to transform competent *E. coli* DH5α. Colonies that contained the 1.1 kb insert were chosen for further analysis. The DNA from the DH5α clones was analyzed by restriction enzyme mapping and the cloning junctions of the chosen plasmids were sequenced. After this analysis, the DNA obtained from the DH5α clones was used to transform *E. coli* BL21(DE3)-ΔompA. The transformants were selected on LB-agar containing 100 μg/ml of carbenicillin. Several transformants were screened for their ability to make the class 2 porin protein. This was done by growing the clones in LB liquid medium containing 100 μg/ml of carbenicillin and 0.4% glucose at 30° C. to $OD_{600}$=0.6 then inducing the cultures with IPTG (0.4 mM). The cells were then disrupted and the cell extract was analyzed by SDS-PAGE.

Example 3 . Cloning and Expression of the Mature Class 3 Porin from Group B *Neisseria meningitidis* Strain 8765 in *E. coli*

Genomic DNA was isolated from approximately 0.5 g of Group B *Neisseria meningitidis* strain 8765 using the method described above (Sambrook et al., *Molecular Cloning: A Laboratory Manual,* 2nd ed., Cold Spring Harbor, N.Y., Cold Spring Harbor Laboratory Press (1989)). This DNA then served as the template for two class 3 porin specific oligonucleotides in a standard PCR reaction.

The mature class 3 porin was constructed by amplifying the genomic DNA from 8765 using the oligonucleotides: (SEQ ID NO. 22) 5' GTT GCA GCA CAT ATG GAC GTT ACC CTG TAC GGC ACC 3' (SEQ ID NO. 23) and 5' GGG GGG ATG GAT CCA GAT TAG AAT TTG TGG CGC AGA CCG ACA CC 3'. This strategy allowed the cloning of the amplified class 3 porin into the NdeI and BamH sites of the plasmid pET-24a(+), thus producing a mature class 3 porin. Standard PCR was conducted using the genomic DNA isolated from 8765 as the template and the two oligonucleotides described above.

The reaction conditions were as follows: 8765 genomic DNA 200 ng, the two oligonucleotide primers described above at 1 μM of each, 200 μM of each dNTP, PCR reaction buffer (10 mM Tris HCl, 50 mM KCl, pH 8.3), 1.5 mM MgCl$_2$, and 2.5 units of Taq polymerase, and made up to 100 μl with distilled water. This reaction mixture was then subjected to 25 cycles of 95° C. for 1 min, 50° C. for 2 min and 72° C. for 1.5 min.

This PCR reaction yielded about 930 bp of product, as analyzed on a 1% agarose gel. The DNA obtained from the PCR reaction was gel purified and digested with the restriction enzymes NdeI and BamHI. The 930 bp product was again gel purified and ligated to NdeI and BamHI digested pET-24a(+) using T4 ligase. This ligation mixture was then used to transform competent E. coli DH5α. Colonies that contained the 930 bp insert were chosen for further analysis. The DNA from the E. coli DH5α clones was analyzed by restriction enzyme mapping and cloning junctions of the chosen plasmids were sequenced. After this analysis, the DNA obtained from the E. coli DH5α clones was used to transform E. coli BL21(DE3)-ΔompA. The transformants were selected on LB-agar contacting 50 μg/ml of kanamycin. Several transformants were screened for their ability to make the class 3 porin protein. This was done by growing the clones in LB liquid medium containing 50 μg/ml of kanamycin and 0.4% of glucose at 30° C. to OD$_{600}$=0.6 then inducing the cultures with IPTG (1 mM). The cells were then disrupted and the cell extract was analyzed by SDS-PAGE.

Example 4. Purification and Refolding of Recombinant Class 2 Porin

E coli strain BL21(DE3)ΔompA [pNV-5] is grown to mid-log phase (OD=0.6 at 600 nm) in Luria broth at 30° C. IPTG is then added (0.4 mM final) and the cells grown an additional two hours at 37° C. The cells were then harvested and washed with several volumes of TEN buffer (50 mM Tris-HCl, 0.2M NaCl, 10 mM EDTA, pH=8.0) and the cell paste stored frozen at −75° C.

For purification preweighed cells are thawed and suspended in TEN buffer at a 1:15 ratio (g/v). The suspension is passed through a Stansted cell disrupter (Stansted fluid power Ltd.) twice at 8,000 psi. The resultant solution is then centrifuged at 13,000 rpm for 20 min and the supernatant discarded. The pellet is then twice suspended in TEN buffer containing 0.5% deoxycholate and the supernatants discarded. The pellet is then suspended in TEN buffer containing 8M deionized urea (electrophoresis grade) and 0.1 mM PMSF (3 g/10 ml). The suspension is sonicated for 10 min or until an even suspension is achieved. 10 ml of a 10% aqueous solution of 3,14-zwittergen (Calbiochem) is added and the solution thoroughly mixed. The solution is again sonicated for 10 min. Any residual insoluble material is removed by centrifugation. The protein concentration is determined and the protein concentration adjusted to 2 mg/ml with 8M urea-10% zwittergen buffer (1:1 ratio).

This mixture is then applied to a 2.6×100 cm column of Sephacryl S-300 equilibrated in 100 mM Tris-HCl, 1M NaCl, 10 mM EDTA, 20 mM CaCl$_2$, 0.05% 3,14-zwittergen, 0.02% sodium azide, pH =8.0. The flow rate is maintained at 1 ml/min. Fractions of 10 ml are collected. The porin refolds into trimer during the gel filtration. The OD=280 nm of each fraction is measured and those fractions containing protein are subjected to SDS gel electrophoresis assay for porin. Those fractions containing porin are pooled. The pooled fractions are either dialyzed or diluted 1:10 in 50 mM Tris HCl pH=8.0, 0.05% 3,14-zwittergen, 5 mM EDTA, 0.1M NaCl. The resulting solution is then applied to a 2.6×10 cm Q sepharose high performance column (Pharmacia) equilibrated in the same buffer. The porin is eluted with a linear gradient of 0.1 to 1M NaCl.

Example 5. Purification and Refolding of Recombinant Class 3 Porin

E coli strain BL21 (DE3) ΔompA containing the porB-pET-17b plasmid is grown to mid-log phase (OD=0.6 at 600 m) in Luria broth at 30° C. IPTG is then added (0.4 mM final) and the cells grown an additional two hours at 37° C. The cells were then harvested and washed with several volumes of TEN buffer (50 mM Tris-HCl, 0.2M NaCl, 10 mM EDTA, pH=8.0) and the cell paste stored frozen at −75° C.

For purification about 3 grams of cells are thawed and suspended in 9 ml of TEN buffer. Lysozyme is added (Sigma, 0.25 mg/ml) deoxycholate (Sigma, 1.3 mg/ml) plus PMSF (Sigma, μg/ml) and the mixture gently shaken for one hour at room temperature. During this time, the cells lyse and the released DNA causes the solution to become very viscous. DNase is then added (Sigma, 2 μg/ml) and the solution again mixed for one hour at room temperature. The mixture is then centrifuged at 15K rpm in a S-600 rotor for 30 minutes and the supernatant discarded. The pellet is then twice suspended in 10 ml of TEN buffer and the supernatants discarded. The pellet is then suspended in 10 ml of 8M urea (Pierce) in TEN buffer. The mixture is gently stirred to break up any clumps. The suspension is sonicated for 20 minutes or until an even suspension is achieved. 10 ml of a 10% aqueous solution of 3,14-zwittergen (Calbiochem) is added and the solution thoroughly mixed. The solution is again sonicated for 10 minutes. Any residual insoluble material is removed by centrifugation. The protein concentration is determined and the protein concentration adjusted to 2 mg/ml with 8M urea-10% zwittergen buffer (1:1 ratio).

This mixture is then applied to a 180×2.5 cm column of Sephacryl S-300 (Pharmacia) equilibrated in 100 mM Tris-HCl, 1M NaCl, 10 mM EDTA, 20 mM CaCl$_2$, 0.05% 3,14-zwittergen, pH=8.0. The flow rate is maintained at 1 ml/min. Fractions of 10 ml are collected. The porin refolds into trimer during the gel filtration. The OD$_{280}$ nm of each fraction is measured and those fractions containing protein are subjected to SDS gel electrophoresis assay for porin. Those fractions containing porin are pooled.

The pooled fractions are dialyzed and concentrated 4–6 fold using Amicon concentrator with a PM 10 membrane against buffer containing 100 mM Tris-HCl, 0.1M NaCl, 10 mM EDTA, 0.05% 3,14-zwittergen, pH =8.0. Alternatively, the pooled fractions are precipitated with 80% ethanol and resuspended with the above-mentioned buffer. Six to 10 mg of the material is then applied to a monoQ 10/10 column (Pharmacia) equilibrated in the same buffer. The porin is eluted from a shallow 0.1 to 0.6M NaCl gradient with a 1.2% increase per min over a 50 min period. The Flow rate is 1 ml/min. The peak containing porin is collected and dialyzed against TEN buffer and 0.05% 3,14-zwittergen. The porin may be purified further by another S-300 chromatography.

Example 6. Purification and Chemical Modification of the Polysaccharides

The capsular polysaccharide from both group B *Neisseria meningitidis* and *E. coli* K1 consists of $\alpha(2\rightarrow8)$ polysialic acid (commonly referred to as GBMP or K1 polysaccharide). High molecular weight polysaccharide isolated from growth medium by precipitation (see, Frasch, C. E., "Production and Control of *Neisseria meningitidis* Vaccines" in *Bacterial Vaccines*, Alan R. Liss, Inc., pages 123–145 (1990)) was purified and chemically modified before being coupled to the porin protein. The high molecular weight polysaccharide was partially depolymerized with 0.1M acetic acid (7 mg polysaccharide/ml), pH=6.0 to 6.5 (70° C., 3 hrs) to provide polysaccharide having an average molecular weight of 12,000–16,000. After purification by gel filtration column chromatography (Superdex 200 prep grade, Pharmacia), the polysaccharide was N-deacetylated in the presence of NaBH$_4$ and then N-propionylated as described by Jennings et al. (*J. Immunol.* 137:1808 (1986)) to afford N—Pr GBMP. Treatment with NaIO$_4$ followed by gel filtration column purification gave the oxidized N—Pr GBMP having an average molecular weight of 12,000 daltons.

Example 7. Coupling of Oxidized N—Pr GBMP to the Group B Meningococcal Class 3 Porin Protein (PP)

The oxidized N—Pr GBMP (9.5 mg) was added to purified class 3 porin protein (3.4 mg) dissolved in 0.21 ml of 0.2M phosphate buffer pH 7.5 which also contained 10% octyl glucoside. After the polysaccharide was dissolved, sodium cyanoborohydride (7 mg) was added and the reaction solution was incubated at 37° C. for 4 days. The reaction mixture was diluted with 0.15M sodium chloride solution containing 0.01% thimerosal and separated by gel filtration column chromatography using Superdex 200 PC. The conjugate (N—Pr GBMP-PP) was obtained as single peak eluting near the void volume. Analysis of the conjugate solution for sialic acid and protein showed that the conjugate consists of 43% polysaccharide by weight. The porin protein was recovered in the conjugate in 44% yield and the polysaccharide in 12% yield. The protein recoveries in different experiments generally occur in the 50–80% range and those of the polysaccharide in the 9–13% range.

Example 8. Immunogenicity Studies

The immunogenicities of the N—Pr GBMP-PP conjugate and those of the N—Pr GBMP-Tetanus toxoid (N—Pr GBMP-TT) conjugate which was prepared by a similar coupling procedure were assayed in 4–6 week old outbread Swiss Webster CFW female mice. The polysaccharide (2 μg)-conjugate was administered on days 1, 14 and 28, and the sera collected on day 38. The conjugates were administered as saline solutions, adsorbed on aluminum hydroxide, or admixed with stearyl tyrosine. The sera ELISA titers against the polysaccharide antigen and bactericidal tilers against *N. meningitidis* group B are summarized in Table 1.

Having now fully described this invention, it will be understood to those of ordinary skill in the an that the same can be performed within a wide and equivalent range of conditions, formulations and other perimeters without affecting the scope of the invention or any embodiment thereof. All patents and publications cited herein are fully incorporated by reference herein in their entirety.

TABLE 1

ELISA and Bactericidal Titers of Group B Meningococcal Conjugate Vaccines (N-Pr GBMP-Protein)

| Vaccine | Adjuvant | ELISA Titer | Bactericidal Titer |
|---|---|---|---|
| N-Pr GBMP-TT | Saline | 5,400 | 0 |
| | Al(OH)$_3$ | 13,000 | 0 |
| | ST[1] | 17,000 | 0 |
| | CFA[2] | 40,000 | 800 |
| N-Pr GBMP-PP | Saline | 20,000 | 500 |
| | Saline | 22,000 | 150 |
| | Saline | 39,000 | 960 |
| | Al(OH)$_3$ | 93,000 | 200 |
| | Al(OH)$_3$ | 166,000 | >3,200 |
| | Al(OH)$_3$ | 130,000 | 1,200 |
| | ST | 53,000 | 1,000 |
| | ST | 29,000 | 1,700 |
| | ST | 72,000 | 1,500 |
| N-Pr GBMP | Saline | >100 | 0 |
| | Al(OH)$_3$ | >100 | 0 |
| | ST | >100 | 0 |
| PP | Saline | >100 | 0 |
| | Al(OH)$_3$ | >100 | 0 |
| | ST | 660 | 0 |

[1]ST = Stearyl tyrosine.
[2]CFA = Complete Freund's Adjuvant

What is claimed is:

1. A method for the high level expression of the outer membrane meningococcal group B porin protein or fusion protein thereof in an *E. coli* host cell having a deleted ompΔ gene (ΔompA), comprising:
(a) transforming the *E. coli* ΔompA host cell with a vector comprising a selectable marker and a gene coding for a protein selected from the group consisting of:
(i) a mature porin protein, and
(ii) a fusion protein which is a mature porin protein fused to amino acids 1 to 22 of the T7 gene φ10 capsid protein;
wherein said gene is operably linked to the T7 promoter;
(b) growing the transformed host cell in a culture medium containing a selection agent, and
(c) inducing expression of said protein;
wherein the protein so expressed comprises more than about 2% of the total protein expressed in the host cell.

2. The method according to claim 1, wherein said protein is the mature group B class 2 porin protein.

3. The method according to claim 1, wherein said protein is the mature group B class 3 porin protein.

4. The method according to claim 1, wherein said protein comprises more than about 30% of the total proteins expressed in the host cell.

5. The method of claim 1, wherein said *E. coli* strain is *E. coli* BL21(DE3)ΔompA.

6. The method of claim 1, wherein said gene codes for a fusion protein which is a mature porin protein fused to amino acids 1 to 22 of the T7 gene φ10 capsid protein.

7. The method of claim 1, wherein said gene codes for a mature porin protein.

8. The method of claim 1, wherein said vector is selected from the group consisting of pET-17b, pET-11a, pET-24a-d(+) and pET-9a.

9. A method of purifying a recombinantly produced outer membrane meningococcal group B porin protein or fusion protein thereof, the method comprising:
(a) lysing *E. coli* ΔompA host cells produced in step (c) of claim 1 to release the protein as insoluble inclusion bodies;
(b) washing said insoluble inclusion bodies with a buffer to remove contaminating *E. coli* cellular proteins;
(c) suspending and dissolving said inclusion bodies in an aqueous solution of a denaturant;
(d) diluting said solution with a detergent; and
(e) purifying said protein by gel filtration and ion exchange chromatography.

10. The method of claim 9, wherein the diluted solution obtained in step (d) has a concentration of less than 10 mg protein/ml.

11. A method of refolding a recombinantly produced outer membrane meningococcal group B porin protein or fusion protein thereof, the method comprising:
(a) lysing *E. coli* host cells capable of expressing the meningococcal group B porin protein to release the protein as insoluble inclusion bodies;
(b) washing said insoluble inclusion bodies with a buffer to remove contaminating *E. coli* cellular proteins;
(c) suspending and dissolving said inclusion bodies in an aqueous solution of a denaturant;
(d) diluting said solution with a detergent; and
(e) passing said diluted solution through a gel filtration column;
whereby folded, trimeric protein is obtained.

12. The method of claim 11, wherein the diluted solution obtained in step (d) has a concentration of less than 10 mg protein/ml.

13. An *E. coli* ΔompA host cell that contains a vector which comprises a DNA molecule coding for a meningococcal group B porin protein or fusion protein thereof operably linked to the T7 promotor of said vector.

14. The *E. coli* strain of claim 13, wherein said DNA molecule codes for the mature meningococcal group B class 2 porin protein.

15. The *E. coli* strain of claim 13, wherein said DNA molecule codes for the mature meningococcal group B class 3 porin protein.

16. The *E. coli* strain of claim 13, wherein said DNA molecule codes for a fusion protein having the amino acid sequence depicted in FIG. 4.

17. The *E. coli* strain of claim 13, wherein said vector is pET-17b.

18. The *E. coli* ΔompA host cell of claim 13, wherein said host cell is *E. coli* strain BL21(DE3) ΔompA.

19. *E. coli* strain BL21(DE3)ΔompA.

* * * * *

UNITED STATES PATENT AND TRADEMARK OFFICE
CERTIFICATE OF CORRECTION

PATENT NO. : 5,439,808

DATED : August 8, 1995

INVENTOR(S): BLAKE et al.

It is certified that error appears in the above-identified patent and that said Letters Patent is hereby corrected as shown below.

On the title page: Item [75] Inventors:

'Milan S. Blake, New York, N.Y." is incorrect and should be replaced with --Milan S. Blake, Iowa City, Ia.--; line 10, "Shu-Mei Liang, Bethesda;" is incorrect and should be replaced with --Shu-Mei Liang, Bethesda, Md.--; and line 11, "Lucjan J.J. Hronowski, Laurel, both of Md." is incorrect and should be replaced with --Lucjan J.J. Hronowski, Norwood, Ma.--.

UNITED STATES PATENT AND TRADEMARK OFFICE
CERTIFICATE OF CORRECTION

PATENT NO. :  5,439,808

DATED      :  August 8, 1995

INVENTOR(S):  BLAKE et al.

It is certified that error appears in the above-identified patent and that said Letters Patent is hereby corrected as shown below.

Column 43, line 35, "ompΔ" is incorrect and should be replaced with --ompA--

Signed and Sealed this

Thirteenth Day of February, 1996

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,439,808

DATED : August 8, 1995

INVENTORS : Milan S. Blake *et al.*

It is certified that an error appears in the above-identified patent and that said Letters Patent is hereby corrected as shown below.

Immediately after the title, please add the following paragraph:

--This invention was made with U.S. government support under AI18367 awarded by NIAID. The U.S. government has certain rights in the invention.--

Signed and Sealed this

Fourth Day of April, 2000

Q. TODD DICKINSON

*Attest:*

*Attesting Officer*  *Director of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 930 base pairs
        ( B ) TYPE: nucleic acid
        ( C ) STRANDEDNESS: double
        ( D ) TOPOLOGY: both ( i x ) FEATURE:
        ( A ) NAME/KEY: CDS
        ( B ) LOCATION: 1..930

( x i ) SEQUENCE DESCRIPTION: SEQ ID NO:1:

```
TTG  TAC  GGT  ACA  ATT  AAA  GCA  GGC  GTA  GAA  ACT  TCC  CGC  TCT  GTA  TTT       48
Leu  Tyr  Gly  Thr  Ile  Lys  Ala  Gly  Val  Glu  Thr  Ser  Arg  Ser  Val  Phe
```

| | 1 | | | 5 | | | | 10 | | | | 15 | | | |
|---|---|---|---|---|---|---|---|---|---|---|---|---|---|---|---|
| CAC | CAG | AAC | GGC | CAA | GTT | ACT | GAA | GTT | ACA | ACC | GCT | ACC | GGC | ATC | GTT | 96 |
| His | Gln | Asn | Gly | Gln | Val | Thr | Glu | Val | Thr | Thr | Ala | Thr | Gly | Ile | Val | |
| | | | 20 | | | | 25 | | | | | 30 | | | | |
| GAT | TTG | GGT | TCG | AAA | ATC | GGC | TTC | AAA | GGC | CAA | GAA | GAC | CTC | GGT | AAC | 144 |
| Asp | Leu | Gly | Ser | Lys | Ile | Gly | Phe | Lys | Gly | Gln | Glu | Asp | Leu | Gly | Asn | |
| | | 35 | | | | 40 | | | | | 45 | | | | | |
| GGC | CTG | AAA | GCC | ATT | TGG | CAG | GTT | GAG | CAA | AAA | GCA | TCT | ATC | GCC | GGT | 192 |
| Gly | Leu | Lys | Ala | Ile | Trp | Gln | Val | Glu | Gln | Lys | Ala | Ser | Ile | Ala | Gly | |
| | 50 | | | | | 55 | | | | | 60 | | | | | |
| ACT | GAC | TCC | GGT | TGG | GGC | AAC | CGC | CAA | TCC | TTC | ATC | GGC | TTG | AAA | GGC | 240 |
| Thr | Asp | Ser | Gly | Trp | Gly | Asn | Arg | Gln | Ser | Phe | Ile | Gly | Leu | Lys | Gly | |
| 65 | | | | | 70 | | | | | 75 | | | | | 80 | |
| GGC | TTC | GGT | AAA | TTG | CGC | GTC | GGT | CGT | TTG | AAC | AGC | GTC | CTG | AAA | GAC | 288 |
| Gly | Phe | Gly | Lys | Leu | Arg | Val | Gly | Arg | Leu | Asn | Ser | Val | Leu | Lys | Asp | |
| | | | | 85 | | | | | 90 | | | | | 95 | | |
| ACC | GGC | GAC | ATC | AAT | CCT | TGG | GAT | AGC | AAA | AGC | GAC | TAT | TTG | GGT | GTA | 336 |
| Thr | Gly | Asp | Ile | Asn | Pro | Trp | Asp | Ser | Lys | Ser | Asp | Tyr | Leu | Gly | Val | |
| | | | 100 | | | | 105 | | | | | 110 | | | | |
| AAC | AAA | ATT | GCC | GAA | CCC | GAG | GCA | CGC | CTC | ATT | TCC | GTA | CGC | TAC | GAT | 384 |
| Asn | Lys | Ile | Ala | Glu | Pro | Glu | Ala | Arg | Leu | Ile | Ser | Val | Arg | Tyr | Asp | |
| | | 115 | | | | 120 | | | | | 125 | | | | | |
| TCT | CCC | GAA | TTT | GCC | GGC | CTC | AGC | GGC | AGC | GTA | CAA | TAC | GCG | CTT | AAC | 432 |
| Ser | Pro | Glu | Phe | Ala | Gly | Leu | Ser | Gly | Ser | Val | Gln | Tyr | Ala | Leu | Asn | |
| | 130 | | | | | 135 | | | | | 140 | | | | | |
| GAC | AAT | GCA | GGC | AGA | CAT | AAC | AGC | GAA | TCT | TAC | CAC | GCC | GGC | TTC | AAC | 480 |
| Asp | Asn | Ala | Gly | Arg | His | Asn | Ser | Glu | Ser | Tyr | His | Ala | Gly | Phe | Asn | |
| 145 | | | | | 150 | | | | | 155 | | | | | 160 | |
| TAC | AAA | AAC | GGT | GGC | TTC | TTC | GTG | CAA | TAT | GGC | GGT | GCC | TAT | AAA | AGA | 528 |
| Tyr | Lys | Asn | Gly | Gly | Phe | Phe | Val | Gln | Tyr | Gly | Gly | Ala | Tyr | Lys | Arg | |
| | | | | 165 | | | | | 170 | | | | | 175 | | |
| CAT | CAT | CAA | GTG | CAA | GAG | GGC | TTG | AAT | ATT | GAG | AAA | TAC | CAG | ATT | CAC | 576 |
| His | His | Gln | Val | Gln | Glu | Gly | Leu | Asn | Ile | Glu | Lys | Tyr | Gln | Ile | His | |
| | | | 180 | | | | 185 | | | | | 190 | | | | |
| CGT | TTG | GTC | AGC | GGT | TAC | GAC | AAT | GAT | GCC | CTG | TAC | GCT | TCC | GTA | GCC | 624 |
| Arg | Leu | Val | Ser | Gly | Tyr | Asp | Asn | Asp | Ala | Leu | Tyr | Ala | Ser | Val | Ala | |
| | | 195 | | | | 200 | | | | | 205 | | | | | |
| GTA | CAG | CAA | CAA | GAC | GCG | AAA | CTG | ACT | GAT | GCT | TCC | AAT | TCG | CAC | AAC | 672 |
| Val | Gln | Gln | Gln | Asp | Ala | Lys | Leu | Thr | Asp | Ala | Ser | Asn | Ser | His | Asn | |
| | 210 | | | | | 215 | | | | | 220 | | | | | |
| TCT | CAA | ACC | GAA | GTT | GCC | GCT | ACC | TTG | GCA | TAC | CGC | TTC | GGC | AAC | GTA | 720 |
| Ser | Gln | Thr | Glu | Val | Ala | Ala | Thr | Leu | Ala | Tyr | Arg | Phe | Gly | Asn | Val | |
| 225 | | | | | 230 | | | | | 235 | | | | | 240 | |
| ACG | CCC | CGA | GTT | TCT | TAC | GCC | CAC | GGC | TTC | AAA | GGT | TTG | GTT | GAT | GAT | 768 |
| Thr | Pro | Arg | Val | Ser | Tyr | Ala | His | Gly | Phe | Lys | Gly | Leu | Val | Asp | Asp | |
| | | | | 245 | | | | | 250 | | | | | 255 | | |
| GCA | GAC | ATA | GGC | AAC | GAA | TAC | GAC | CAA | GTG | GTT | GTC | GGT | GCG | GAA | TAC | 816 |
| Ala | Asp | Ile | Gly | Asn | Glu | Tyr | Asp | Gln | Val | Val | Val | Gly | Ala | Glu | Tyr | |
| | | | 260 | | | | 265 | | | | | 270 | | | | |
| GAC | TTC | TCC | AAA | CGC | ACT | TCT | GCC | TTG | GTT | TCT | GCC | GGT | TGG | TTG | CAA | 864 |
| Asp | Phe | Ser | Lys | Arg | Thr | Ser | Ala | Leu | Val | Ser | Ala | Gly | Trp | Leu | Gln | |
| | | 275 | | | | 280 | | | | | 285 | | | | | |
| GAA | GGC | AAA | GGC | GAA | AAC | AAA | TTC | GTA | GCG | ACT | GCC | GGC | GGT | GTT | GGT | 912 |
| Glu | Gly | Lys | Gly | Glu | Asn | Lys | Phe | Val | Ala | Thr | Ala | Gly | Gly | Val | Gly | |
| | 290 | | | | | 295 | | | | | 300 | | | | | |
| CTG | CGT | CAC | AAA | TTC | TAA | | | | | | | | | | | 930 |
| Leu | Arg | His | Lys | Phe | | | | | | | | | | | | |
| 305 | | | | | 310 | | | | | | | | | | | |

( 2 ) INFORMATION FOR SEQ ID NO:2:

( i ) SEQUENCE CHARACTERISTICS:

(A) LENGTH: 309 amino acids
(B) TYPE: amino acid
(D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Leu | Tyr | Gly | Thr | Ile | Lys | Ala | Gly | Val | Glu | Thr | Ser | Arg | Ser | Val | Phe |
| 1 | | | | 5 | | | | | 10 | | | | | 15 |
| His | Gln | Asn | Gly | Gln | Val | Thr | Glu | Val | Thr | Thr | Ala | Thr | Gly | Ile | Val |
| | | | 20 | | | | | 25 | | | | | 30 | | |
| Asp | Leu | Gly | Ser | Lys | Ile | Gly | Phe | Lys | Gly | Gln | Glu | Asp | Leu | Gly | Asn |
| | | | 35 | | | | 40 | | | | | 45 | | | |
| Gly | Leu | Lys | Ala | Ile | Trp | Gln | Val | Glu | Gln | Lys | Ala | Ser | Ile | Ala | Gly |
| | 50 | | | | | 55 | | | | | 60 | | | | |
| Thr | Asp | Ser | Gly | Trp | Gly | Asn | Arg | Gln | Ser | Phe | Ile | Gly | Leu | Lys | Gly |
| 65 | | | | | 70 | | | | | 75 | | | | | 80 |
| Gly | Phe | Gly | Lys | Leu | Arg | Val | Gly | Arg | Leu | Asn | Ser | Val | Leu | Lys | Asp |
| | | | | 85 | | | | | 90 | | | | | 95 | |
| Thr | Gly | Asp | Ile | Asn | Pro | Trp | Asp | Ser | Lys | Ser | Asp | Tyr | Leu | Gly | Val |
| | | | 100 | | | | | 105 | | | | | 110 | | |
| Asn | Lys | Ile | Ala | Glu | Pro | Glu | Ala | Arg | Leu | Ile | Ser | Val | Arg | Tyr | Asp |
| | | 115 | | | | | 120 | | | | | 125 | | | |
| Ser | Pro | Glu | Phe | Ala | Gly | Leu | Ser | Gly | Ser | Val | Gln | Tyr | Ala | Leu | Asn |
| | 130 | | | | | 135 | | | | | 140 | | | | |
| Asp | Asn | Ala | Gly | Arg | His | Asn | Ser | Glu | Ser | Tyr | His | Ala | Gly | Phe | Asn |
| 145 | | | | | 150 | | | | | 155 | | | | | 160 |
| Tyr | Lys | Asn | Gly | Gly | Phe | Phe | Val | Gln | Tyr | Gly | Gly | Ala | Tyr | Lys | Arg |
| | | | | 165 | | | | | 170 | | | | | 175 | |
| His | His | Gln | Val | Gln | Glu | Gly | Leu | Asn | Ile | Glu | Lys | Tyr | Gln | Ile | His |
| | | | 180 | | | | | 185 | | | | | 190 | | |
| Arg | Leu | Val | Ser | Gly | Tyr | Asp | Asn | Asp | Ala | Leu | Tyr | Ala | Ser | Val | Ala |
| | | 195 | | | | | 200 | | | | | 205 | | | |
| Val | Gln | Gln | Gln | Asp | Ala | Lys | Leu | Thr | Asp | Ala | Ser | Asn | Ser | His | Asn |
| | 210 | | | | | 215 | | | | | 220 | | | | |
| Ser | Gln | Thr | Glu | Val | Ala | Ala | Thr | Leu | Ala | Tyr | Arg | Phe | Gly | Asn | Val |
| 225 | | | | | 230 | | | | | 235 | | | | | 240 |
| Thr | Pro | Arg | Val | Ser | Tyr | Ala | His | Gly | Phe | Lys | Gly | Leu | Val | Asp | Asp |
| | | | | 245 | | | | | 250 | | | | | 255 | |
| Ala | Asp | Ile | Gly | Asn | Glu | Tyr | Asp | Gln | Val | Val | Val | Gly | Ala | Glu | Tyr |
| | | | 260 | | | | | 265 | | | | | 270 | | |
| Asp | Phe | Ser | Lys | Arg | Thr | Ser | Ala | Leu | Val | Ser | Ala | Gly | Trp | Leu | Gln |
| | | 275 | | | | | 280 | | | | | 285 | | | |
| Glu | Gly | Lys | Gly | Glu | Asn | Lys | Phe | Val | Ala | Thr | Ala | Gly | Gly | Val | Gly |
| | 290 | | | | | 295 | | | | | 300 | | | | |
| Leu | Arg | His | Lys | Phe | | | | | | | | | | | |
| 305 | | | | | | | | | | | | | | | |

(2) INFORMATION FOR SEQ ID NO:3:

(i) SEQUENCE CHARACTERISTICS:
(A) LENGTH: 1029 base pairs
(B) TYPE: nucleic acid
(C) STRANDEDNESS: double
(D) TOPOLOGY: both (ix) FEATURE:
(A) NAME/KEY: CDS
(B) LOCATION: 1..1029

(xi) SEQUENCE DESCRIPTION: SEQ ID NO:3:

-continued

| | | | | | | | | | | | | | | | | |
|---|---|---|---|---|---|---|---|---|---|---|---|---|---|---|---|---|
| ATG | GAC | GTT | ACC | TTG | TAC | GGT | ACA | ATT | AAA | GCA | GGC | GTA | GAA | GTT | TCT | 48 |
| Met | Asp | Val | Thr | Leu | Tyr | Gly | Thr | Ile | Lys | Ala | Gly | Val | Glu | Val | Ser | |
| 1 | | | | 5 | | | | | 10 | | | | | 15 | | |
| CGC | GTA | AAA | GAT | GCT | GGT | ACA | TAT | AAA | GCT | CAA | GGC | GGA | AAA | TCT | AAA | 96 |
| Arg | Val | Lys | Asp | Ala | Gly | Thr | Tyr | Lys | Ala | Gln | Gly | Gly | Lys | Ser | Lys | |
| | | | 20 | | | | | 25 | | | | | 30 | | | |
| ACT | GCA | ACC | CAA | ATT | GCC | GAC | TTC | GGT | TCT | AAA | ATC | GGT | TTC | AAA | GGT | 144 |
| Thr | Ala | Thr | Gln | Ile | Ala | Asp | Phe | Gly | Ser | Lys | Ile | Gly | Phe | Lys | Gly | |
| | | 35 | | | | | 40 | | | | | 45 | | | | |
| CAA | GAA | GAC | CTC | GGC | AAC | GGC | ATG | AAA | GCC | ATT | TGG | CAG | TTG | GAA | CAA | 192 |
| Gln | Glu | Asp | Leu | Gly | Asn | Gly | Met | Lys | Ala | Ile | Trp | Gln | Leu | Glu | Gln | |
| | 50 | | | | | 55 | | | | | 60 | | | | | |
| AAA | GCC | TCC | ATC | GCC | GGT | ACT | AAC | AGC | GGC | TGG | GGT | AAC | CGC | CAG | TCC | 240 |
| Lys | Ala | Ser | Ile | Ala | Gly | Thr | Asn | Ser | Gly | Trp | Gly | Asn | Arg | Gln | Ser | |
| 65 | | | | | 70 | | | | | 75 | | | | | 80 | |
| TTC | ATC | GGC | TTG | AAA | GGC | GGC | TTC | GGT | ACC | GTC | CGC | GCC | GGT | AAT | CTG | 288 |
| Phe | Ile | Gly | Leu | Lys | Gly | Gly | Phe | Gly | Thr | Val | Arg | Ala | Gly | Asn | Leu | |
| | | | | 85 | | | | | 90 | | | | | 95 | | |
| AAC | ACC | GTA | TTG | AAA | GAC | AGC | GGC | GAC | AAC | GTC | AAT | GCA | TGG | GAA | TCT | 336 |
| Asn | Thr | Val | Leu | Lys | Asp | Ser | Gly | Asp | Asn | Val | Asn | Ala | Trp | Glu | Ser | |
| | | | 100 | | | | | 105 | | | | | 110 | | | |
| GGT | TCT | AAC | ACC | GAA | GAT | GTA | CTG | GGA | CTG | GGT | ACT | ATC | GGT | CGT | GTA | 384 |
| Gly | Ser | Asn | Thr | Glu | Asp | Val | Leu | Gly | Leu | Gly | Thr | Ile | Gly | Arg | Val | |
| | | 115 | | | | | 120 | | | | | 125 | | | | |
| GAA | AGC | CGT | GAA | ATC | TCC | GTA | CGC | TAC | GAC | TCT | CCC | GTA | TTT | GCA | GGC | 432 |
| Glu | Ser | Arg | Glu | Ile | Ser | Val | Arg | Tyr | Asp | Ser | Pro | Val | Phe | Ala | Gly | |
| | 130 | | | | | 135 | | | | | 140 | | | | | |
| TTC | AGC | GGC | AGC | GTA | CAA | TAC | GTT | CCG | CGC | GAT | AAT | GCG | AAT | GAT | GTG | 480 |
| Phe | Ser | Gly | Ser | Val | Gln | Tyr | Val | Pro | Arg | Asp | Asn | Ala | Asn | Asp | Val | |
| 145 | | | | | 150 | | | | | 155 | | | | | 160 | |
| GAT | AAA | TAC | AAA | CAT | ACG | AAG | TCC | AGC | CGT | GAG | TCT | TAC | CAC | GCC | GGT | 528 |
| Asp | Lys | Tyr | Lys | His | Thr | Lys | Ser | Ser | Arg | Glu | Ser | Tyr | His | Ala | Gly | |
| | | | | 165 | | | | | 170 | | | | | 175 | | |
| CTG | AAA | TAC | GAA | AAT | GCC | GGT | TTC | TTC | GGT | CAA | TAC | GCA | GGT | TCT | TTT | 576 |
| Leu | Lys | Tyr | Glu | Asn | Ala | Gly | Phe | Phe | Gly | Gln | Tyr | Ala | Gly | Ser | Phe | |
| | | | 180 | | | | | 185 | | | | | 190 | | | |
| GCC | AAA | TAT | GCT | GAT | TTG | AAC | ACT | GAT | GCA | GAA | CGT | GTT | GCA | GTA | AAT | 624 |
| Ala | Lys | Tyr | Ala | Asp | Leu | Asn | Thr | Asp | Ala | Glu | Arg | Val | Ala | Val | Asn | |
| | | 195 | | | | | 200 | | | | | 205 | | | | |
| ACT | GCA | AAT | GCC | CAT | CCT | GTT | AAG | GAT | TAC | CAA | GTA | CAC | CGC | GTA | GTT | 672 |
| Thr | Ala | Asn | Ala | His | Pro | Val | Lys | Asp | Tyr | Gln | Val | His | Arg | Val | Val | |
| | 210 | | | | | 215 | | | | | 220 | | | | | |
| GCC | GGT | TAC | GAT | GCC | AAT | GAC | CTG | TAC | GTT | TCT | GTT | GCC | GGT | CAG | TAT | 720 |
| Ala | Gly | Tyr | Asp | Ala | Asn | Asp | Leu | Tyr | Val | Ser | Val | Ala | Gly | Gln | Tyr | |
| 225 | | | | | 230 | | | | | 235 | | | | | 240 | |
| GAA | GCT | GCT | AAA | AAC | AAC | GAG | GTT | GGT | TCT | ACC | AAG | GGT | AAA | AAA | CAC | 768 |
| Glu | Ala | Ala | Lys | Asn | Asn | Glu | Val | Gly | Ser | Thr | Lys | Gly | Lys | Lys | His | |
| | | | | 245 | | | | | 250 | | | | | 255 | | |
| GAG | CAA | ACT | CAA | GTT | GCC | GCT | ACT | GCC | GCT | TAC | CGT | TTT | GGC | AAC | GTA | 816 |
| Glu | Gln | Thr | Gln | Val | Ala | Ala | Thr | Ala | Ala | Tyr | Arg | Phe | Gly | Asn | Val | |
| | | | 260 | | | | | 265 | | | | | 270 | | | |
| ACG | CCT | CGC | GTT | TCT | TAC | GCC | CAC | GGC | TTC | AAA | GCT | AAA | GTG | AAT | GGC | 864 |
| Thr | Pro | Arg | Val | Ser | Tyr | Ala | His | Gly | Phe | Lys | Ala | Lys | Val | Asn | Gly | |
| | | 275 | | | | | 280 | | | | | 285 | | | | |
| GTG | AAA | GAC | GCA | AAT | TAC | CAA | TAC | GAC | CAA | GTT | ATC | GTT | GGT | GCC | GAC | 912 |
| Val | Lys | Asp | Ala | Asn | Tyr | Gln | Tyr | Asp | Gln | Val | Ile | Val | Gly | Ala | Asp | |
| | 290 | | | | | 295 | | | | | 300 | | | | | |
| TAC | GAC | TTC | TCC | AAA | CGC | ACT | TCC | GCT | CTG | GTT | TCT | GCC | GGT | TGG | TTG | 960 |
| Tyr | Asp | Phe | Ser | Lys | Arg | Thr | Ser | Ala | Leu | Val | Ser | Ala | Gly | Trp | Leu | |
| 305 | | | | | 310 | | | | | 315 | | | | | 320 | |
| AAA | CAA | GGT | AAA | GGC | GCG | GGA | AAA | GTC | GAA | CAA | ACT | GCC | AGC | ATG | GTT | 1008 |

```
Lys Gln Gly Lys Gly Ala Gly Lys Val Glu Gln Thr Ala Ser Met Val
                325                 330                 335

GGT CTG CGT CAC AAA TTC TAA                                                          1029
Gly Leu Arg His Lys Phe
            340
```

(2) INFORMATION FOR SEQ ID NO:4:

(i) SEQUENCE CHARACTERISTICS:
       (A) LENGTH: 342 amino acids
       (B) TYPE: amino acid
       (D) TOPOLOGY: linear (ii) MOLECULE TYPE: protein (xi) SEQUENCE DESCRIPTION: SEQ ID NO:4:

```
Met Asp Val Thr Leu Tyr Gly Thr Ile Lys Ala Gly Val Glu Val Ser
 1               5                  10                  15

Arg Val Lys Asp Ala Gly Thr Tyr Lys Ala Gln Gly Gly Lys Ser Lys
                20                  25                  30

Thr Ala Thr Gln Ile Ala Asp Phe Gly Ser Lys Ile Gly Phe Lys Gly
            35                  40                  45

Gln Glu Asp Leu Gly Asn Gly Met Lys Ala Ile Trp Gln Leu Glu Gln
 50                  55                  60

Lys Ala Ser Ile Ala Gly Thr Asn Ser Gly Trp Gly Asn Arg Gln Ser
 65                  70                  75                  80

Phe Ile Gly Leu Lys Gly Gly Phe Gly Thr Val Arg Ala Gly Asn Leu
                85                  90                  95

Asn Thr Val Leu Lys Asp Ser Gly Asp Asn Val Asn Ala Trp Glu Ser
                100                 105                 110

Gly Ser Asn Thr Glu Asp Val Leu Gly Leu Gly Thr Ile Gly Arg Val
            115                 120                 125

Glu Ser Arg Glu Ile Ser Val Arg Tyr Asp Ser Pro Val Phe Ala Gly
            130                 135                 140

Phe Ser Gly Ser Val Gln Tyr Val Pro Arg Asp Asn Ala Asn Asp Val
145                 150                 155                 160

Asp Lys Tyr Lys His Thr Lys Ser Ser Arg Glu Ser Tyr His Ala Gly
                165                 170                 175

Leu Lys Tyr Glu Asn Ala Gly Phe Phe Gly Gln Tyr Ala Gly Ser Phe
                180                 185                 190

Ala Lys Tyr Ala Asp Leu Asn Thr Asp Ala Glu Arg Val Ala Val Asn
                195                 200                 205

Thr Ala Asn Ala His Pro Val Lys Asp Tyr Gln Val His Arg Val Val
210                 215                 220

Ala Gly Tyr Asp Ala Asn Asp Leu Tyr Val Ser Val Ala Gly Gln Tyr
225                 230                 235                 240

Glu Ala Ala Lys Asn Asn Glu Val Gly Ser Thr Lys Gly Lys Lys His
                245                 250                 255

Glu Gln Thr Gln Val Ala Ala Thr Ala Ala Tyr Arg Phe Gly Asn Val
            260                 265                 270

Thr Pro Arg Val Ser Tyr Ala His Gly Phe Lys Ala Lys Val Asn Gly
            275                 280                 285

Val Lys Asp Ala Asn Tyr Gln Tyr Asp Gln Val Ile Val Gly Ala Asp
            290                 295                 300

Tyr Asp Phe Ser Lys Arg Thr Ser Ala Leu Val Ser Ala Gly Trp Leu
305                 310                 315                 320

Lys Gln Gly Lys Gly Ala Gly Lys Val Glu Gln Thr Ala Ser Met Val
                325                 330                 335
```

Gly Leu Arg His Lys Phe
340

( 2 ) INFORMATION FOR SEQ ID NO:5:

( i ) SEQUENCE CHARACTERISTICS:
    ( A ) LENGTH: 1092 base pairs
    ( B ) TYPE: nucleic acid
    ( C ) STRANDEDNESS: double
    ( D ) TOPOLOGY: both ( i x ) FEATURE:
    ( A ) NAME/KEY: CDS
    ( B ) LOCATION: 1..1092

( x i ) SEQUENCE DESCRIPTION: SEQ ID NO:5:

| ATG | GCT | AGC | ATG | ACT | GGT | GGA | CAG | CAA | ATG | GGT | CGG | GAT | TCA | AGC | TTG | 48 |
| Met | Ala | Ser | Met | Thr | Gly | Gly | Gln | Gln | Met | Gly | Arg | Asp | Ser | Ser | Leu | |
| 1 | | | | 5 | | | | | 10 | | | | | 15 | | |

| GTA | CCG | AGC | TCG | GAT | CCA | GAC | GTT | ACC | TTG | TAC | GGT | ACA | ATT | AAA | GCA | 96 |
| Val | Pro | Ser | Ser | Asp | Pro | Asp | Val | Thr | Leu | Tyr | Gly | Thr | Ile | Lys | Ala | |
| | | | 20 | | | | | 25 | | | | | 30 | | | |

| GGC | GTA | GAA | GTT | TCT | CGC | GTA | AAA | GAT | GCT | GGT | ACA | TAT | AAA | GCT | CAA | 144 |
| Gly | Val | Glu | Val | Ser | Arg | Val | Lys | Asp | Ala | Gly | Thr | Tyr | Lys | Ala | Gln | |
| | | | 35 | | | | 40 | | | | | 45 | | | | |

| GGC | GGA | AAA | TCT | AAA | ACT | GCA | ACC | CAA | ATT | GCC | GAC | TTC | GGT | TCT | AAA | 192 |
| Gly | Gly | Lys | Ser | Lys | Thr | Ala | Thr | Gln | Ile | Ala | Asp | Phe | Gly | Ser | Lys | |
| | 50 | | | | | 55 | | | | | 60 | | | | | |

| ATC | GGT | TTC | AAA | GGT | CAA | GAA | GAC | CTC | GGC | AAC | GGC | ATG | AAA | GCC | ATT | 240 |
| Ile | Gly | Phe | Lys | Gly | Gln | Glu | Asp | Leu | Gly | Asn | Gly | Met | Lys | Ala | Ile | |
| 65 | | | | | 70 | | | | | 75 | | | | | 80 | |

| TGG | CAG | TTG | GAA | CAA | AAA | GCC | TCC | ATC | GCC | GGC | ACT | AAC | AGC | GGC | TGG | 288 |
| Trp | Gln | Leu | Glu | Gln | Lys | Ala | Ser | Ile | Ala | Gly | Thr | Asn | Ser | Gly | Trp | |
| | | | | 85 | | | | | 90 | | | | | 95 | | |

| GGT | AAC | CGC | CAG | TCC | TTC | ATC | GGC | TTG | AAA | GGC | GGC | TTC | GGT | ACC | GTC | 336 |
| Gly | Asn | Arg | Gln | Ser | Phe | Ile | Gly | Leu | Lys | Gly | Gly | Phe | Gly | Thr | Val | |
| | | | 100 | | | | | 105 | | | | | 110 | | | |

| CGC | GCC | GGT | AAT | CTG | AAC | ACC | GTA | TTG | AAA | GAC | AGC | GGC | GAC | AAC | GTC | 384 |
| Arg | Ala | Gly | Asn | Leu | Asn | Thr | Val | Leu | Lys | Asp | Ser | Gly | Asp | Asn | Val | |
| | | 115 | | | | | 120 | | | | | 125 | | | | |

| AAT | GCA | TGG | GAA | TCT | GGT | TCT | AAC | ACC | GAA | GAT | GTA | CTG | GGA | CTG | GGT | 432 |
| Asn | Ala | Trp | Glu | Ser | Gly | Ser | Asn | Thr | Glu | Asp | Val | Leu | Gly | Leu | Gly | |
| | 130 | | | | | 135 | | | | | 140 | | | | | |

| ACT | ATC | GGT | CGT | GTA | GAA | AGC | CGT | GAA | ATC | TCC | GTA | CGC | TAC | GAC | TCT | 480 |
| Thr | Ile | Gly | Arg | Val | Glu | Ser | Arg | Glu | Ile | Ser | Val | Arg | Tyr | Asp | Ser | |
| 145 | | | | | 150 | | | | | 155 | | | | | 160 | |

| CCC | GTA | TTT | GCA | GGC | TTC | AGC | GGC | AGC | GTA | CAA | TAC | GTT | CCG | CGC | GAT | 528 |
| Pro | Val | Phe | Ala | Gly | Phe | Ser | Gly | Ser | Val | Gln | Tyr | Val | Pro | Arg | Asp | |
| | | | | 165 | | | | | 170 | | | | | 175 | | |

| AAT | GCG | AAT | GAT | GTG | GAT | AAA | TAC | AAA | CAT | ACG | AAG | TCC | AGC | CGT | GAG | 576 |
| Asn | Ala | Asn | Asp | Val | Asp | Lys | Tyr | Lys | His | Thr | Lys | Ser | Ser | Arg | Glu | |
| | | | 180 | | | | | 185 | | | | | 190 | | | |

| TCT | TAC | CAC | GCC | GGT | CTG | AAA | TAC | GAA | AAT | GCC | GGT | TTC | TTC | GGT | CAA | 624 |
| Ser | Tyr | His | Ala | Gly | Leu | Lys | Tyr | Glu | Asn | Ala | Gly | Phe | Phe | Gly | Gln | |
| | | 195 | | | | | 200 | | | | | 205 | | | | |

| TAC | GCA | GGT | TCT | TTT | GCC | AAA | TAT | GCT | GAT | TTG | AAC | ACT | GAT | GCA | GAA | 672 |
| Tyr | Ala | Gly | Ser | Phe | Ala | Lys | Tyr | Ala | Asp | Leu | Asn | Thr | Asp | Ala | Glu | |
| | 210 | | | | | 215 | | | | | 220 | | | | | |

| CGT | GTT | GCA | GTA | AAT | ACT | GCA | AAT | GCC | CAT | CCT | GTT | AAG | GAT | TAC | CAA | 720 |
| Arg | Val | Ala | Val | Asn | Thr | Ala | Asn | Ala | His | Pro | Val | Lys | Asp | Tyr | Gln | |
| 225 | | | | | 230 | | | | | 235 | | | | | 240 | |

| GTA | CAC | CGC | GTA | GTT | GCC | GGT | TAC | GAT | GCC | AAT | GAC | CTG | TAC | GTT | TCT | 768 |
| Val | His | Arg | Val | Val | Ala | Gly | Tyr | Asp | Ala | Asn | Asp | Leu | Tyr | Val | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
|GTT|GCC|GGT|CAG|TAT|GAA|GCT|GCT|AAA|AAC|AAC|GAG|GTT|GGT|TCT|ACC|816|
|Val|Ala|Gly|Gln 260|Tyr|Glu|Ala|Ala|Lys 265|Asn|Asn|Glu|Val|Gly 270|Ser|Thr| |
|AAG|GGT|AAA|AAA|CAC|GAG|CAA|ACT|CAA|GTT|GCC|GCT|ACT|GCC|GCT|TAC|864|
|Lys|Gly|Lys 275|Lys|His|Glu|Gln 280|Thr|Gln|Val|Ala|Ala 285|Thr|Ala|Ala|Tyr| |
|CGT|TTT|GGC|AAC|GTA|ACG|CCT|CGC|GTT|TCT|TAC|GCC|CAC|GGC|TTC|AAA|912|
|Arg|Phe 290|Gly|Asn|Val|Thr|Pro 295|Arg|Val|Ser|Tyr|Ala 300|His|Gly|Phe|Lys| |
|GCT|AAA|GTG|AAT|GGC|GTG|AAA|GAC|GCA|AAT|TAC|CAA|TAC|GAC|CAA|GTT|960|
|Ala 305|Lys|Val|Asn|Gly|Val 310|Lys|Asp|Ala|Asn|Tyr 315|Gln|Tyr|Asp|Gln|Val 320| |
|ATC|GTT|GGT|GCC|GAC|TAC|GAC|TTC|TCC|AAA|CGC|ACT|TCC|GCT|CTG|GTT|1008|
|Ile|Val|Gly|Ala|Asp 325|Tyr|Asp|Phe|Ser|Lys 330|Arg|Thr|Ser|Ala|Leu 335|Val| |
|TCT|GCC|GGT|TGG|TTG|AAA|CAA|GGT|AAA|GGC|GCG|GGA|AAA|GTC|GAA|CAA|1056|
|Ser|Ala|Gly|Trp 340|Leu|Lys|Gln|Gly|Lys 345|Gly|Ala|Gly|Lys|Val 350|Glu|Gln| |
|ACT|GCC|AGC|ATG|GTT|GGT|CTG|CGT|CAC|AAA|TTC|TAA| | | | |1092|
|Thr|Ala|Ser|Met 355|Val|Gly|Leu|Arg|His 360|Lys|Phe| | | | | | |

(2) INFORMATION FOR SEQ ID NO:6:

(i) SEQUENCE CHARACTERISTICS:
(A) LENGTH: 363 amino acids
(B) TYPE: amino acid
(D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
|Met 1|Ala|Ser|Met|Thr 5|Gly|Gly|Gln|Gln|Met 10|Gly|Arg|Asp|Ser|Ser 15|Leu|
|Val|Pro|Ser|Ser 20|Asp|Pro|Asp|Val|Thr 25|Leu|Tyr|Gly|Thr|Ile 30|Lys|Ala|
|Gly|Val|Glu 35|Val|Ser|Arg|Val|Lys 40|Asp|Ala|Gly|Thr|Tyr 45|Lys|Ala|Gln|
|Gly|Gly 50|Lys|Ser|Lys|Thr|Ala 55|Thr|Gln|Ile|Ala|Asp 60|Phe|Gly|Ser|Lys|
|Ile 65|Gly|Phe|Lys|Gly|Gln 70|Glu|Asp|Leu|Gly|Asn 75|Gly|Met|Lys|Ala|Ile 80|
|Trp|Gln|Leu|Glu|Gln 85|Lys|Ala|Ser|Ile|Ala 90|Gly|Thr|Asn|Ser|Gly 95|Trp|
|Gly|Asn|Arg|Gln 100|Ser|Phe|Ile|Gly|Leu 105|Lys|Gly|Gly|Phe|Gly 110|Thr|Val|
|Arg|Ala|Gly 115|Asn|Leu|Asn|Thr|Val 120|Leu|Lys|Asp|Ser|Gly 125|Asp|Asn|Val|
|Asn|Ala 130|Trp|Glu|Ser|Gly|Ser 135|Asn|Thr|Glu|Asp|Val 140|Leu|Gly|Leu|Gly|
|Thr 145|Ile|Gly|Arg|Val|Glu 150|Ser|Arg|Glu|Ile|Ser 155|Val|Arg|Tyr|Asp|Ser 160|
|Pro|Val|Phe|Ala|Gly 165|Phe|Ser|Gly|Ser|Val 170|Gln|Tyr|Val|Pro|Arg 175|Asp|
|Asn|Ala|Asn|Asp 180|Val|Asp|Lys|Tyr|Lys 185|His|Thr|Lys|Ser|Ser 190|Arg|Glu|
|Ser|Tyr|His 195|Ala|Gly|Leu|Lys|Tyr 200|Glu|Asn|Ala|Gly|Phe 205|Phe|Gly|Gln|
|Tyr|Ala 210|Gly|Ser|Phe|Ala|Lys 215|Tyr|Ala|Asp|Leu|Asn 220|Thr|Asp|Ala|Glu|

| | | | | | | | | | | | | | | |
|---|---|---|---|---|---|---|---|---|---|---|---|---|---|---|
| Arg | Val | Ala | Val | Asn | Thr | Ala | Asn | Ala | His | Pro | Val | Lys | Asp | Tyr | Gln |
| 225 | | | | 230 | | | | 235 | | | | | | 240 |
| Val | His | Arg | Val | Val | Ala | Gly | Tyr | Asp | Ala | Asn | Asp | Leu | Tyr | Val | Ser |
| | | | | 245 | | | | 250 | | | | | 255 | |
| Val | Ala | Gly | Gln | Tyr | Glu | Ala | Ala | Lys | Asn | Asn | Glu | Val | Gly | Ser | Thr |
| | | | 260 | | | | | 265 | | | | | 270 | | |
| Lys | Gly | Lys | Lys | His | Glu | Gln | Thr | Gln | Val | Ala | Ala | Thr | Ala | Ala | Tyr |
| | | 275 | | | | | 280 | | | | | 285 | | | |
| Arg | Phe | Gly | Asn | Val | Thr | Pro | Arg | Val | Ser | Tyr | Ala | His | Gly | Phe | Lys |
| | 290 | | | | | 295 | | | | | 300 | | | | |
| Ala | Lys | Val | Asn | Gly | Val | Lys | Asp | Ala | Asn | Tyr | Gln | Tyr | Asp | Gln | Val |
| 305 | | | | | 310 | | | | 315 | | | | | | 320 |
| Ile | Val | Gly | Ala | Asp | Tyr | Asp | Phe | Ser | Lys | Arg | Thr | Ser | Ala | Leu | Val |
| | | | | 325 | | | | | 330 | | | | | 335 | |
| Ser | Ala | Gly | Trp | Leu | Lys | Gln | Gly | Lys | Gly | Ala | Gly | Lys | Val | Glu | Gln |
| | | | 340 | | | | | 345 | | | | | 350 | | |
| Thr | Ala | Ser | Met | Val | Gly | Leu | Arg | His | Lys | Phe | | | | | |
| | | 355 | | | | | 360 | | | | | | | | |

( 2 ) INFORMATION FOR SEQ ID NO:7:

( i ) SEQUENCE CHARACTERISTICS:
        ( A ) LENGTH: 187 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 101..187

( x i ) SEQUENCE DESCRIPTION: SEQ ID NO:7:

```
AGATCTCGAT  CCCGCGAAAT  TAATACGACT  CACTATAGGG  AGACCACAAC  GGTTTCCCTC      60

TAGAAATAAT  TTTGTTTAAC  TTAAAGAAGG  AGATATACAT ATG GCT AGC ATG ACT         115
                                               Met Ala Ser Met Thr
                                                 1               5

GGT GGA CAG CAA ATG GGT CGG GAT TCA AGC TTG GTA CCG AGC TCG GAT            163
Gly Gly Gln Gln Met Gly Arg Asp Ser Ser Leu Val Pro Ser Ser Asp
             10                  15                  20

CTG CAG GTT ACC TTG TAC GGT ACA                                            187
Leu Gln Val Thr Leu Tyr Gly Thr
             25
```

( 2 ) INFORMATION FOR SEQ ID NO:8:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Ala | Ser | Met | Thr | Gly | Gly | Gln | Gln | Met | Gly | Arg | Asp | Ser | Ser | Leu |
| 1 | | | | 5 | | | | | 10 | | | | | 15 | |
| Val | Pro | Ser | Ser | Asp | Leu | Gln | Val | Thr | Leu | Tyr | Gly | Thr | | | |
| | | | 20 | | | | | 25 | | | | | | | |

( 2 ) INFORMATION FOR SEQ ID NO:9:

( i ) SEQUENCE CHARACTERISTICS:
        ( A ) LENGTH: 54 base pairs
        ( B ) TYPE: nucleic acid
        ( C ) STRANDEDNESS: both
        ( D ) TOPOLOGY: both ( i x ) FEATURE:
    ( A ) NAME/KEY: CDS
    ( B ) LOCATION: 1..24

( x i ) SEQUENCE DESCRIPTION: SEQ ID NO:9:

```
GTT GGT CTG CGT CAC AAA TTC TAACTCGAGC AGATCCGGCT GCTAACAAAG      51
Val Gly Leu Arg His Lys Phe
 1               5

CCC                                                                54
```

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Val Gly Leu Arg His Lys Phe
 1               5
```

( 2 ) INFORMATION FOR SEQ ID NO:11:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
GGGGTAGATC TGCAGGTTAC CTTGTACGGT ACAATTAAAG CAGGCGT               47
```

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GGGGGGGTGA CCCTCGAGTT AGAATTTGTG ACGCAGACCA AC                    42
```

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TCAAGCTTGG TACCGAGCTC                                             20
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
TTTGTTAGCA GCCGGATCTG                                             20
```

( 2 ) INFORMATION FOR SEQ ID NO:15:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

CTCAAGACCC GTTTAGAGGC C    21

( 2 ) INFORMATION FOR SEQ ID NO:16:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

AGCGGCTTGG AATTCCCGGC TGGCTTAAAT TTC    33

( 2 ) INFORMATION FOR SEQ ID NO:17:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

CAAACGAATG AATTCAAATA AAAAGCCTG    30

( 2 ) INFORMATION FOR SEQ ID NO:18:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

CCTGTTGCAG CACATATGGA CGTTACCTTG TACGGTACAA TTAAAGC    47

( 2 ) INFORMATION FOR SEQ ID NO:19:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

CGACAGGCTT TTTCTCGAGA CCAATCTTTT CAG    33

( 2 ) INFORMATION FOR SEQ ID NO:20:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CCTGTTGCAG CGGATCCAGA CGTTACCTTG TACGGTACAA TTAAAGC    47

( 2 ) INFORMATION FOR SEQ ID NO:21:

( i ) SEQUENCE CHARACTERISTICS:
    ( A ) LENGTH: 33 base pairs
    ( B ) TYPE: nucleic acid (C) STRANDEDNESS: single
(D) TOPOLOGY: linear (xi) SEQUENCE DESCRIPTION: SEQ ID NO:21:

CGACAGGCTT TTTCTCGAGA CCAATCTTTT CAG  33

(2) INFORMATION FOR SEQ ID NO:22:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:22:

GTTGCAGCAC ATATGGACGT TACCCTGTAC GGCACC  36

(2) INFORMATION FOR SEQ ID NO:23:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:23:

GGGGGGATGG ATCCAGATTA GAATTTGTGG CGCAGACCGA CACC  44